United States Patent
Bergheim et al.

(10) Patent No.: US 11,968,669 B2
(45) Date of Patent: Apr. 23, 2024

(54) SCHEDULING DATABASE SYSTEM

(71) Applicants: TDO Software, Inc., San Diego, CA (US); Bjarne Bergheim, Laguna Hills, CA (US); Sean Doonan, San Diego, CA (US); Gary B. Carr, Rancho Santa Fe, CA (US); Luiz A. Motta, San Diego, CA (US); Zoltan Iles, Carlsbad, CA (US); Russell Tarvin, Oceanside, CA (US)

(72) Inventors: Bjarne Bergheim, Laguna Hills, CA (US); Sean Doonan, San Diego, CA (US); Gary B. Carr, Rancho Santa Fe, CA (US); Luiz A. Motta, San Diego, CA (US); Zoltan Iles, Carlsbad, CA (US); Russell Tarvin, Oceanside, CA (US)

(73) Assignee: TDO Software, Inc., San Diego, CA (US)

( * ) Notice: Subject to any disclaimer, the term of this patent is extended or adjusted under 35 U.S.C. 154(b) by 190 days.

(21) Appl. No.: 17/416,425

(22) PCT Filed: Dec. 18, 2019

(86) PCT No.: PCT/US2019/067286
§ 371 (c)(1),
(2) Date: Jun. 18, 2021

(87) PCT Pub. No.: WO2020/132143
PCT Pub. Date: Jun. 25, 2020

(65) Prior Publication Data
US 2022/0078829 A1    Mar. 10, 2022

Related U.S. Application Data

(60) Provisional application No. 62/860,162, filed on Jun. 11, 2019, provisional application No. 62/831,464, (Continued)

(51) Int. Cl.
*H04W 72/54* (2023.01)
*H04W 72/121* (2023.01)
*H04W 72/20* (2023.01)

(52) U.S. Cl.
CPC ......... *H04W 72/20* (2023.01); *H04W 72/121* (2013.01); *H04W 72/54* (2023.01)

(58) Field of Classification Search
CPC ..... H04W 72/04; H04W 72/20; H04W 72/54; H04W 72/12; H04W 72/121;
(Continued)

(56) References Cited

U.S. PATENT DOCUMENTS 5,860,067 A * 1/1999 Onda .................... G06Q 10/109
715/963
6,335,927 B1 * 1/2002 Elliott ................... H04L 63/083
370/352

(Continued)

OTHER PUBLICATIONS

International Search Report and Written Opinion dated Feb. 27, 2020, in International Application No. PCT/US2019/067286 filed Dec. 18, 2019; in 16 pages.

(Continued)

*Primary Examiner* — Jenee Holland
(74) *Attorney, Agent, or Firm* — Knobbe, Martens, Olson & Bear, LLP

(57) ABSTRACT

Systems and methods are provided for database scheduling. Scheduling entries are created and stored in a central database and an entity's database. In response to a user request to view the availability of the entity, a scheduling system can
(Continued)

retrieve the scheduling data of an entity from the central database. The scheduling database system attempts to connect to an entity to propagate a scheduling entry in near time. If a connection to the entity from the scheduling database system can be made, the system updates the entity's database in near time. However, an attempted connection may have a fail status due to network issues and/or a VPN connection being unavailable. If a connection is unavailable, the updated scheduling data is propagated via a synchronization process. In the scheduling database system, a scheduling entry in the central scheduling database includes a synchronization status that marks the scheduling entry for future propagation. A synchronization status is set in the entities' database(s) to mark an entry for synchronization purposes. The scheduling database system permits double booking.

20 Claims, 26 Drawing Sheets

Related U.S. Application Data filed on Apr. 9, 2019, provisional application No. 62/798,347, filed on Jan. 29, 2019, provisional application No. 62/787,705, filed on Jan. 2, 2019, provisional application No. 62/782,234, filed on Dec. 19, 2018.

(58) Field of Classification Search
CPC ............... H04W 28/10; H04W 28/065; H04W 52/0216; H04W 76/28; H04L 47/10
See application file for complete search history.

(56) References Cited

U.S. PATENT DOCUMENTS

| | | | |
|---|---|---|---|
| 7,119,828 B1* | 10/2006 | Kizhnerman | H04M 3/56 348/E7.083 |
| 7,643,420 B2* | 1/2010 | Kwan | H04L 47/10 370/235 |
| 8,161,288 B2* | 4/2012 | Newman | H04L 63/104 713/182 |
| 9,864,485 B2 | 1/2018 | Patton et al. | |
| 10,120,746 B1* | 11/2018 | Sharifi Mehr | H04L 63/1425 |
| 10,121,301 B1* | 11/2018 | Ren | G07C 9/00896 |
| 10,561,560 B2 | 2/2020 | Boutoussov et al. | |
| 11,173,010 B2 | 11/2021 | Boutoussov et al. | |
| 11,202,687 B2 | 12/2021 | Boutoussov et al. | |
| 2004/0073924 A1* | 4/2004 | Pendakur | H04N 21/4622 348/E7.071 |
| 2007/0242738 A1* | 10/2007 | Park | H04W 28/0252 375/224 |
| 2008/0040501 A1* | 2/2008 | Harrang | H04L 67/30 709/232 |
| 2008/0126989 A1* | 5/2008 | Flores | H04N 21/4143 715/833 |
| 2011/0029664 A1* | 2/2011 | Harrang | H04B 17/309 709/224 |
| 2014/0249878 A1* | 9/2014 | Kaufman | G06Q 10/1095 705/7.19 |
| 2014/0278679 A1* | 9/2014 | Navani | G06Q 10/06311 705/7.19 |
| 2018/0279397 A1* | 9/2018 | Faccin | H04W 76/11 |
| 2018/0358123 A1* | 12/2018 | Silver | G06F 16/958 |
| 2020/0014486 A1* | 1/2020 | Harrang | H04L 47/263 |

OTHER PUBLICATIONS

International Preliminary Report on Patentability dated Jun. 16, 2021, in International Application No. PCT/US2019/067286 filed Dec. 18, 2019; in 9 pages.

Wright et al. "Memorandum Report: Excluded Individuals Employed by Service Providers in Medicaid Managed Care Networks, OEI-07-09-00632." In: Office of Inspector General. Sep. 27, 2012 (Sep. 27, 2012) Retrieved on Feb. 14, 2020 (Feb. 14, 2020) from <https://oig.hhs.gov/oei/reports/oei-07-09-00632.pdf> entire document.

* cited by examiner

*— 266*

Login to your account to schedule an appointment:
Create an Account

EMAIL

PASSWORD

Forgot Your Password?                                    Continue

SCHEDULING DATABASE SYSTEM

INCORPORATION BY REFERENCE TO ANY PRIORITY APPLICATIONS

This application claims benefit of U.S. Provisional Patent Application Ser. No. 62/782,234 entitled "Patient Workflow And Referral Management System" filed Dec. 19, 2018, U.S. Provisional Patent Application Ser. No. 62/787,705 entitled "Scheduling Database System" filed Jan. 2, 2019, U.S. Provisional Patent Application Ser. No. 62/798,347 entitled "Image Collage Graphical User Interface And Generator" filed Jan. 29, 2019, U.S. Provisional Patent Application Ser. No. 62/831,464 entitled "Scheduling Database System" filed Apr. 9, 2019, and U.S. Provisional Patent Application Ser. No. 62/860,162 entitled "Scheduling Database System" filed Jun. 11, 2019, which are hereby incorporated by reference in their entireties.

BACKGROUND

In a scheduling context, an individual may want to schedule an appointment with an entity, such as a specialist. In some existing systems, in response to a user request to view the availability of the entity, a central system can synchronously retrieve the scheduling data of an entity, such as by retrieving scheduling data in real time or near time. If a user requests to view the availability of multiple entities (e.g., the availability of offices within a hundred-mile radius), then a synchronous approach would make a user wait while the central system makes multiple synchronous calls or requests to the multiple entities to retrieve scheduling data. A central system can connect with entities using a virtual private network, which can introduce further latency to communications between the central system and the entities.

Some existing systems allow an individual to search for entities. The individual can then call the entity to schedule an appointment. In other cases, the individual can see a general practitioner first, and then the general practitioner can provide a referral to the individual. Again, the individual can call the specialist referral to schedule the appointment. Each entity might have its own system or method for managing appointments.

SUMMARY

The systems, methods, and devices described herein each have several aspects, no single one of which is solely responsible for its desirable attributes. Without limiting the scope of this disclosure, several non-limiting features will now be discussed briefly.

According to an embodiment, a method is disclosed comprising: receiving, via a first scheduling input user interface, first login information; determining a first profile associated with the first login information; receiving, via the first scheduling input user interface, a first scheduling search preference; determining, from a plurality of entities, a first subset of entities according to the first scheduling search preference, wherein to determine the first subset of entities further comprises: determining that the first profile lacks authorization for a first entity of the plurality of entities, wherein the first subset of entities excludes the first entity; retrieving first scheduling data for the first subset of entities; causing presentation of a first scheduling user interface, wherein the first scheduling user interface presents the first scheduling data; receiving, via a second scheduling input user interface, second login information; determining a second profile associated with the second login information; receiving, via the second scheduling input user interface, a second scheduling search preference; determining, from the plurality of entities, a second subset of entities according to the second scheduling search preference, wherein to determine the second subset of entities further comprises: determining that the second profile has authorization for the first entity, wherein the second subset of entities comprises the first entity; retrieving second scheduling data for the second subset of entities that includes the first entity; and causing presentation of a second scheduling user interface, wherein the second scheduling user interface presents the second scheduling data.

According to an aspect, the method may further comprise: receiving, via the second scheduling user interface, a scheduling selection for the first entity; determining that an attempted connection with the first entity has a failed status; and storing, in a first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

According to another aspect, the method may further comprise: determining to synchronize the first scheduling entry based at least in part on the first synchronization status of the first scheduling entry; and causing a second scheduling entry to be stored or updated in a second data store of the first entity, the second scheduling entry corresponding to the first scheduling entry.

According to yet another aspect, the method may further comprise: receiving, via the second scheduling user interface, a scheduling selection for the first entity; storing, in a first data store, a first scheduling entry for the first entity according to the scheduling selection, wherein the first scheduling entry further comprises a first synchronization status; determining to synchronize the first scheduling entry based at least in part on the first synchronization status of the first scheduling entry; and causing a second scheduling entry to be stored or updated in a second data store of the first entity, the second scheduling entry corresponding to the first scheduling entry.

According to yet another aspect, the method may further comprise: setting, in the first data store, a first field in a third scheduling entry to a second synchronization status, wherein the second synchronization status marks the third scheduling entry for a synchronization check from an entity to the first data store; determining that the third scheduling entry has a corresponding entry in the second data store of the first entity; and updating, in the first data store, the first field in the third scheduling entry from the second synchronization status to a third synchronization status, the third synchronization status indicating a synchronization complete status.

According to yet another aspect, the method may further comprise: setting, in the first data store, a second field in a fourth scheduling entry to the second synchronization status; determining that an entry in the second data store of the first entity does not exist that corresponds to the fourth scheduling entry; determining to preserve the third scheduling entry based at least in part on the first field being set to the third synchronization status; determining to delete the fourth scheduling entry based at least in part on the second field being set to the second synchronization status; and deleting, in the first data store, the fourth scheduling entry.

According to yet another aspect, the method may further comprise: receiving, via the second scheduling user interface, a scheduling selection for the first entity; and updating a schedule for the first entity according to the scheduling selection.

According to yet another aspect, updating the schedule for the first entity according to the scheduling selection may further comprise: causing a schedule entry to update in a scheduling database for the first entity.

According to yet another aspect, determining that the first profile lacks authorization for the first entity may further comprise: determining that the first profile corresponds to a profile for a person.

According to yet another aspect, determining that the second profile has authorization for the first entity may further comprise: determining that the second profile corresponds to a general practitioner.

According to yet another aspect, determining that the second profile has authorization for the first entity may further comprise: determining that the second profile corresponds to at least one preferred referrer for the first entity.

According to yet another aspect, the method may further comprise: calculating a first number of referrals from the second profile to the first entity; calculating a second number of referrals from another profile to the first entity; determining that the first number of referrals is greater than the second number of referrals; and designating the second profile as the least one preferred referrer for the first entity.

According to yet another aspect, the first entity can correspond to a special practitioner.

According to yet another aspect, the first entity can further correspond to an endodontist.

According to an embodiment, a system is disclosed comprising: a non-transitory computer storage medium configured to at least store computer-executable instructions; and one or more computer hardware processors in communication with the non-transitory computer storage medium, the one or more computer hardware processors configured to execute the computer-executable instructions to at least: receive, via a first scheduling input user interface, first login information; determine a first profile associated with the first login information; receive, via the first scheduling input user interface, a first scheduling search preference; determine, from a plurality of entities, a first subset of entities according to the first scheduling search preference, wherein to determine the first subset of entities further comprises: determine that the first profile lacks authorization for a first entity of the plurality of entities, wherein the first subset of entities excludes the first entity; retrieve first scheduling data for the first subset of entities; cause presentation of a first scheduling user interface comprising the first scheduling data; receive, via a second scheduling input user interface, second login information; determine a second profile associated with the second login information; receive, via the second scheduling input user interface, a second scheduling search preference; determine, from the plurality of entities, a second subset of entities according to the second scheduling search preference, wherein to determine the second subset of entities further comprises: determine that the second profile has authorization for the first entity, wherein the second subset of entities comprises the first entity; retrieve second scheduling data for the second subset of entities that includes the first entity; and cause presentation of a second scheduling user interface comprising the second scheduling data.

According to an aspect, wherein to determine that the first profile lacks authorization for the first entity may further comprise: determine that the first profile corresponds to a profile for a person.

According to another aspect, wherein to determine that the second profile has authorization for the first entity may further comprise: determine that the second profile corresponds to a general practitioner.

According to yet another aspect, wherein to determine that the second profile has authorization for the first entity may further comprise: determine that the second profile corresponds to at least one preferred referrer for the first entity.

According to yet another aspect, the one or more computer hardware processors may be further configured to: calculate a first number of referrals from the second profile to the first entity; calculate a second number of referrals from another profile to the first entity; determine that the first number of referrals is greater than the second number of referrals; and designate the second profile as the least one preferred referrer for the first entity.

According to yet another aspect, the first entity can correspond to a special practitioner.

According to yet another aspect, the first entity can correspond to an endodontist.

According to yet another aspect, the system may further comprise a first data store, wherein the one or more computer hardware processors may be further configured to: receive, via the second scheduling user interface, a scheduling selection for the first entity; determine that an attempted connection with the first entity has a failed status; and store; in a first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

According to yet another aspect, the one or more computer hardware processors may be further configured to: determine to synchronize the first scheduling entry based at least in part on the first synchronization status of the first scheduling entry; and cause a second scheduling entry to be stored or updated in a second data store of the first entity, the second scheduling entry corresponding to the first scheduling entry.

According to yet another aspect, the system may further comprise a first data store, wherein the one or more computer hardware processors may be further configured to: receive, via the second scheduling user interface, a scheduling selection for the first entity; store, in the first data store, a first scheduling entry for the first entity according to the scheduling selection, wherein the first scheduling entry further comprises a first synchronization status; determine to synchronize the first scheduling entry based at least in part on the first synchronization status of the first scheduling entry; and cause a second scheduling entry to be stored or updated in a second data store of the first entity, the second scheduling entry corresponding to the first scheduling entry.

According to yet another aspect, the one or more computer hardware processors may be further configured to: set, in the first data store, a first field in a third scheduling entry to a second synchronization status, wherein the second synchronization status marks the third scheduling entry for a synchronization check from an entity to the first data store; determine that the third scheduling entry has a corresponding entry in the second data store of the first entity; and update, in the first data store, the first field in the third scheduling entry from the second synchronization status to a third synchronization status, the third synchronization status indicating a synchronization complete status.

According to yet another aspect, the one or more computer hardware processors may be further configured to: set, in the first data store, a second field in a fourth scheduling entry to the second synchronization status; determine that an entry in the second data store of the first entity does not exist that corresponds to the fourth scheduling entry; determine to delete the fourth scheduling entry based at least in part on the second field being set to the second synchronization status; and delete, in the first data store, the fourth scheduling entry.

According to yet another aspect, the one or more computer hardware processors may be further configured to: receive, via the second scheduling user interface, a scheduling selection for the first entity; and update a schedule for the first entity according to the scheduling selection.

According to yet another aspect, to update the schedule for the first entity according to the scheduling selection may further comprise: cause a schedule entry to update in a scheduling database for the first entity.

According to an embodiment, a system is disclosed comprising: a non-transitory computer storage medium configured to at least store computer-executable instructions; and one or more computer hardware processors in communication with the non-transitory computer storage medium, the one or more computer hardware processors configured to execute the computer-executable instructions to at least: receive, via a scheduling input user interface, login information; determine a profile associated with the login information; receive, via the scheduling input user interface, a scheduling search preference; determine, from a plurality of entities, a subset of entities according to the scheduling search preference, wherein to determine the subset of entities further comprises: determine that the profile has authorization for a first entity, wherein the subset of entities comprises the first entity; retrieve scheduling data for the subset of entities that includes the first entity; and cause presentation of a scheduling user interface, wherein the scheduling user interface presents the scheduling data.

According to an aspect, the system may further comprise a first data store, wherein the one or more computer hardware processors may be further configured to: receive, via the scheduling user interface, a scheduling selection for the first entity; determine that an attempted connection with the first entity has a failed status; and store, in the first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

According to another aspect, the one or more computer hardware processors may be further configured to: determine to synchronize the first scheduling entry based at least in part on the first synchronization status of the first scheduling entry; and cause a second scheduling entry to be stored or updated in a second data store of the first entity, the second scheduling entry corresponding to the first scheduling entry.

According to yet another aspect, the system may further comprise a first data store, wherein the one or more computer hardware processors may be further configured to: receive, via the scheduling user interface, a scheduling selection for the first entity; store, in the first data store, a first scheduling entry for the first entity according to the scheduling selection, wherein the first scheduling entry further comprises a first synchronization status; determine to synchronize the first scheduling entry based at least in part on the first synchronization status of the first scheduling entry; and cause a second scheduling entry to be stored or updated in a second data store of the first entity, the second scheduling entry corresponding to the first scheduling entry.

According to yet another aspect, the one or more computer hardware processors may be further configured to: set, in the first data store, a first field in a third scheduling entry to a second synchronization status, wherein the second synchronization status marks the third scheduling entry for a synchronization check from an entity to the first data store; determine that the third scheduling entry has a corresponding entry in the second data store of the first entity; and update, in the first data store, the first field in the third scheduling entry from the second synchronization status to a third synchronization status, the third synchronization status indicating a synchronization complete status.

According to yet another aspect, the one or more computer hardware processors may be further configured to: set, in the first data store, a second field in a fourth scheduling entry to the second synchronization status; determine that an entry in the second data store of the first entity does not exist that corresponds to the fourth scheduling entry; determine to delete the fourth scheduling entry based at least in part on the second field being set to the second synchronization status; and delete, in the first data store, the fourth scheduling entry.

According to yet another aspect, the one or more computer hardware processors may be further configured to: receive, via a second scheduling input user interface, second login information; determine a second profile associated with the second login information; receive, via the second scheduling input user interface, a second scheduling search preference; determine, from the plurality of entities, a second subset of entities according to the second scheduling search preference, wherein to determine the second subset of entities further comprises: determine that the second profile lacks authorization for the first entity, wherein the second subset of entities excludes the first entity; retrieve second scheduling data for the second subset of entities; and cause presentation of a second scheduling user interface comprising the second scheduling data.

According to yet another aspect, wherein to determine that the second profile lacks authorization for the first entity may further comprise: determine that the first profile corresponds to a profile for a person.

According to another aspect, wherein to determine that the profile has authorization for the first entity may further comprise: determine that the profile corresponds to a general practitioner.

According to yet another aspect, wherein to determine that the profile has authorization for the first entity may further comprise: determine that the profile corresponds to at least one preferred referrer for the first entity.

According to yet another aspect, the one or more computer hardware processors may be further configured to: calculate a first number of referrals from the profile to the first entity; calculate a second number of referrals from another profile to the first entity; determine that the first number of referrals is greater than the second number of referrals; and designate the profile as the least one preferred referrer for the first entity.

According to yet another aspect, the first entity can correspond to a special practitioner.

According to yet another aspect, the first entity can correspond to an endodontist.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters can denote corresponding features throughout similar embodiments. The following is a brief description of each of the drawings.

FIGS. 2A, 2B, 2C, 2D, 2E, 2F, 2G, 2H, and 2I depict example graphical user interfaces of a scheduling database system, according to some embodiments of the present disclosure.

DETAILED DESCRIPTION

Overview

Figure 1A:
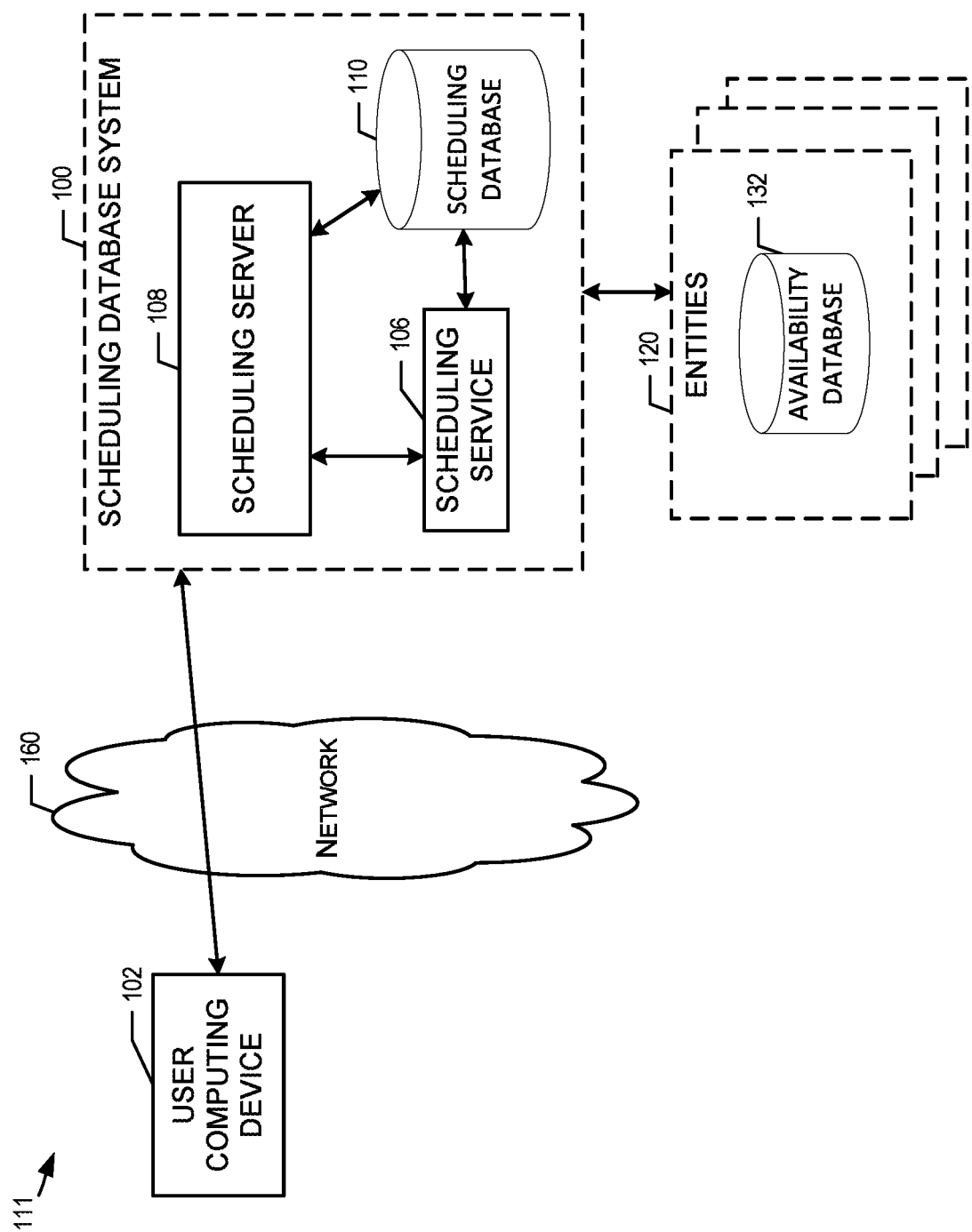
FIG. 1A illustrates a scheduling database system, according to some embodiments of the present disclosure.

As described above, an individual may want to schedule an appointment with an entity, such as a specialist. Sometimes the individual can search for entities within a certain geographical area. However, the individual may be required to call the entity to schedule the appointment. Further, if the individual has not seen a general practitioner first, it may be possible that they do not even need a specialist appointment due to a faulty self-diagnosis. Thus, some specialists may prefer to refuse appointments from individuals that have not seen a general practitioner beforehand to avoid wasting a specialist's time. Some specialist may even prefer to receive referrals from an exclusive subset of referring entities. Thus, existing scheduling systems and/or practices can have certain limitations, such as lacking the ability to efficiently schedule appointments and/or to take into account the preferences of the entities that receive referrals.

Disclosed herein are systems and methods that may be used to advantageously improve scheduling. A user can use a graphical user interface to schedule an appointment. The appointment can be made by the user on their own behalf (such as a user scheduling their own appointment) or can be made by the user on behalf of another (such as a general practitioner scheduling a specialist appointment for an individual in the context of a referral). The user can provide scheduling preferences that can be used by a scheduling system, such as a scheduling database system. The scheduling system can receive input, such as the provided preferences and/or other input, to output scheduling information to be presented to the user. Other scheduling input can include the preferences of the entities receiving referrals. Thus, the scheduling system can apply scheduling logic to determine highly customizable scheduling options based on the provided input. User selected appointments can be booked directly into respective entities' schedules via the scheduling system. The scheduling systems described herein, such as a scheduling database system, can also be referred to herein as a Referral Magnification (or Management) System (RMS) or a Referral Communication Network (RCN). The scheduling systems can provide insight into possible referral options and/or can advantageously facilitate referral appointments.

Disclosed herein are systems and methods for a distributed scheduling system. In response to a user request to view the availability of the entity, a scheduling database system can retrieve the scheduling data of an entity from a local database that is different from the entity's database. Scheduling entries can be created and stored in a central database and an entity's database. In response to a user request to create a scheduling entry through the central system, the system can attempt to connect to an entity to propagate a scheduling entry in near time. If a connection to the entity from the scheduling database system can be made, the system updates the entity's database in near time. However, an attempted connection may have a fail status due to network issues and/or a VPN connection being unavailable. If a connection is unavailable, the updated scheduling data can be propagated via a synchronization process. In the scheduling database system, a scheduling entry in the central scheduling database can include a synchronization status that marks the scheduling entry for future propagation. A synchronization status can be set in one or more entity databases to mark an entry for synchronization purposes. The scheduling database system can permit double booking.

As mentioned above, existing systems and/or practices for scheduling can be very manual and cumbersome for users. Users may be required to schedule appointments with limited insight into the availabilities and/or preferences of the entities. Thus, current systems and/or practices for scheduling can be inefficient for users. From the perspective of an entity, some existing systems and/or practices for scheduling do not allow entities that receive referrals to have much, if any, control over various aspects of the scheduling process. Each entity may also maintain its own scheduling system or database, which may make standardizing the scheduling process across multiple entities difficult. Thus, current systems and/or practices for scheduling can be inefficient for entities.

Accordingly, the systems and techniques described herein may improve computer scheduling and/or database technology. A scheduling database system can use input parameter(s), such as the preferences of particular entities, to accurately and/or efficiently determine scheduling results. For example, an entity that receives referrals may identify a preference to only receive referrals by referring entities that are within the top three referrers for that entity or based on some other criteria. The scheduling database system can dynamically determine those entities that are authorized and can respond to the request for scheduling information accordingly based on the identity of the referring entity. As another example, an entity that receives referrals can specify a preference to only receive referrals from general practitioners. If an individual is requesting scheduling information for specialists, the scheduling database system can filter out scheduling information for those entities that only want general practitioner referrals. Thus, the systems, techniques, and/or algorithms disclosed herein can improve computer scheduling and/or database technology by efficiently providing customized results in some cases. Likewise, the systems, techniques, and/or algorithms described herein can enable users to access data faster, perform analyses faster, and/or interact with one or more user interfaces faster than existing systems.

FIG. 1A illustrates a scheduling database system 100, according to some embodiments of the present disclosure. In the embodiment of FIG. 1A, the computing environment 111 can include a network 160, a scheduling database system 100, a user computing device 102, and one or more entities 120. Various communications between these devices are illustrated. For example, the user computing device 102 may send user input, such as user selections or parameters, to the scheduling database system 100. The user computing device 102 may enable a user to interact with a graphical user interface, such as the graphical user interfaces 200, 230, 260, 266, 268, 272, 276, 278, and 286 of FIGS. 2A, 2B, 2C, 2D, 2E, 2F, 2G, 2H, and 2I, respectively.

The scheduling database system 100 can include a scheduling service 106, a scheduling server 108, and a scheduling database 110. The scheduling server 108 can cause presentation of a graphical user interface, as described herein. The scheduling server 108 can receive user interaction data from the user computing device 102, The scheduling server 108 may communicate with the scheduling service 106, such as by requesting scheduling data and/or transmitting scheduling confirmations. The scheduling server 108 may also communicate directly with the scheduling database 110, such as by executing queries to retrieve scheduling related data, Scheduling data can be stored in the scheduling database 110. The scheduling service 106 can access some data from the scheduling database 110 and/or the database(s) 132, such as data related to availability and/or entity preferences. The scheduling database system 100 may communicate with the one or more entities 120, such as by requesting availability data and/or entity preferences. The scheduling database 110 and/or the database(s) 132 can include scheduling entries that each represent an appointment. Each scheduling entry can be a row or data item in the scheduling database 110 and/or the database(s) 132.

As used herein, in addition to having its ordinary and customary meaning and/or any other implied meaning and in addition to being construed broadly, the term "entity" or "entities" refers to an organization or person, such as a practitioner or a practitioner's office that can receive appointments. In a dental context, example entities are general practitioners or special practitioners. Example special practitioners include, but are not limited to, endodontists, oral surgeons, pediatric dentists, or periodontists. The entities can use practice management software solutions, such as TDO™ Practice Management Software, TDO™ Cloud, or TDO™ Mobile offered by TDO Software, Inc. Entities are described in further detail herein, such as with respect to FIGS. 1A and 1B. A practice management software solution and/or a practice management database system can also be referred to herein as "TDO" or "TDO Cloud."

Additionally, in some embodiments, the scheduling database system 100 and/or practice management software solution can be implemented by one or more virtual machines implemented in a hosted computing environment. The hosted computing environment may include one or more rapidly provisioned and/or released computing resources. The computing resources may include hardware computing, networking and/or storage devices configured with specifically configured computer-executable instructions. A hosted computing environment may also be referred to as a "cloud" or distributed computing environment.

The entities 120 can include scheduling availability database(s) 132. Each entity can include its own respective scheduling availability database 132. As described herein, each respective entity can use practice management software solutions that allow the entity to integrate with the scheduling database system 100. In some embodiments, the scheduling database system 100 can communicate with the entities using a secure communication protocol, such as, but not limited to, a virtual private network ("VPN"). In some embodiments, the scheduling database system 100 can synchronize and/or propagate scheduling data to and/or from the scheduling database 110 and the availability database(s) 132.

The scheduling database 110 and/or the database(s) 132 can include any data structure (and/or combinations of multiple data structures) for storing and/or organizing data, including, but not limited to, relational databases (e.g., Oracle databases, mySQL databases, Microsoft SQL Server databases, Microsoft Azure SQL databases, etc.), non-relational databases (e.g., NoSQL databases, etc.), in-memory databases, spreadsheets, as comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores. The terms "database," "table," and "data source" may be used interchangeably in the present disclosure.

A data store can include computer readable non-transitory storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc), and/or the like. Another example of a data store is a hosted storage environment that includes a collection of physical data storage devices that may be remotely accessible and may be rapidly provisioned as needed (commonly referred to as "cloud" storage).

As described herein, a database of an entity can store the entity's scheduling data. In response to a user request to view the availability of the entity, a scheduling system can synchronously retrieve the scheduling data of an entity, such as by retrieving scheduling data in real time or near time. However, such an approach may be time consuming and/or may have resiliency issues. If a user requests to view the availability of multiple entities (e.g., the availability of offices within a hundred-mile radius), then a synchronous approach would make a user wait while the system makes multiple synchronous calls or requests to the multiple entities to retrieve scheduling data, which may introduce significant delay that may be unacceptable for users of the scheduling system and/or may degrade the user experience. As described above with respect to FIG. 1A, a scheduling system can communicate with an entity using a secure communication protocol, such as, but not limited to, a VPN. Further, secure communication protocols, such as, a VPN, may add latency due to added encryption and/or because data may be routed through a VPN server. Moreover, if a connection (such as a VPN connection) between the scheduling system and the entity is not working, then the scheduling system, under a synchronous approach, may be unable to show the availability of the entity that has the broken connection.

Accordingly, the systems, techniques, and/or algorithms disclosed herein may improve computer scheduling and/or database technology. For example, scheduling data can be distributed among a central scheduling database and an entity's scheduling database, Which can be synchronized over time with an asynchronous process. Thus, appointments stored in a central scheduling database can be propagated to and/or from respective scheduling databases of entities. Advantages of such an approach can include improved response times to schedule appointments and/or increased resiliency. For example, when a user is scheduling an appointment, the scheduling database system simply has to query its own database for the availability of one or more entities instead of having to synchronously connect to the one or more entities. As another example, if a connection between an entity's scheduling database and the scheduling database system is not working, then the scheduling database system can continue to schedule appointments because the system can use its localized database for scheduling purposes and/or any scheduling changes can be propagated to one or more corresponding entities when the connection is working again. Thus, request and response times for querying and scheduling appointments can be reduced and/or querying and scheduling appointments can be resilient to communication failures between the scheduling database system and the one or more entities. Accordingly, the systems and techniques described herein may improve computer scheduling and/or database technology.

In some embodiments, the systems and methods described herein can improve image and/or collage generation. As described above, dentists often give presentations about interesting cases or share those cases with other dentists, which can include images from those cases. Dentists can use word processing programs, image editing programs, or presentation programs to assemble images for presentation or sharing purposes. Using the programs, dentists manually arrange images for presentation or sharing. Manual arrangement of the images can be slow and cumbersome.

Disclosed herein are systems and methods that may be used to advantageously improve image generation. A collage image generator can enable a user to select multiple images, select a template format, and the collage image generator can generate multiple output collage images based on the number of images and format selected. The collage image generator allows a dentist to annotate the output collage images. The output collage can be associated with a patient and can be stored in a searchable database. The output collage can be posted to forums, social media, or electronically transmitted to other entities.

As mentioned above, existing systems and/or practices for generating collage or presentation materials can be very manual and cumbersome for users. For example, word processing programs, image editing programs, or presentation programs, may be slow and cumbersome for users to create multiple page collages. Further, existing systems may be slow and cumbersome for users to prepare collages that are suitable for presentations or for sharing purposes.

The systems and techniques described herein can improve graphical user interfaces. The graphical user interfaces for collage image generation can enable users to access data faster, perform analyses faster, and/or interact with one or more user interfaces faster than existing graphical user interface systems (such as by reducing the number of clicks or selections by a user). Thus, the systems and techniques described herein can improve over conventional user interfaces.

Figure 1B:
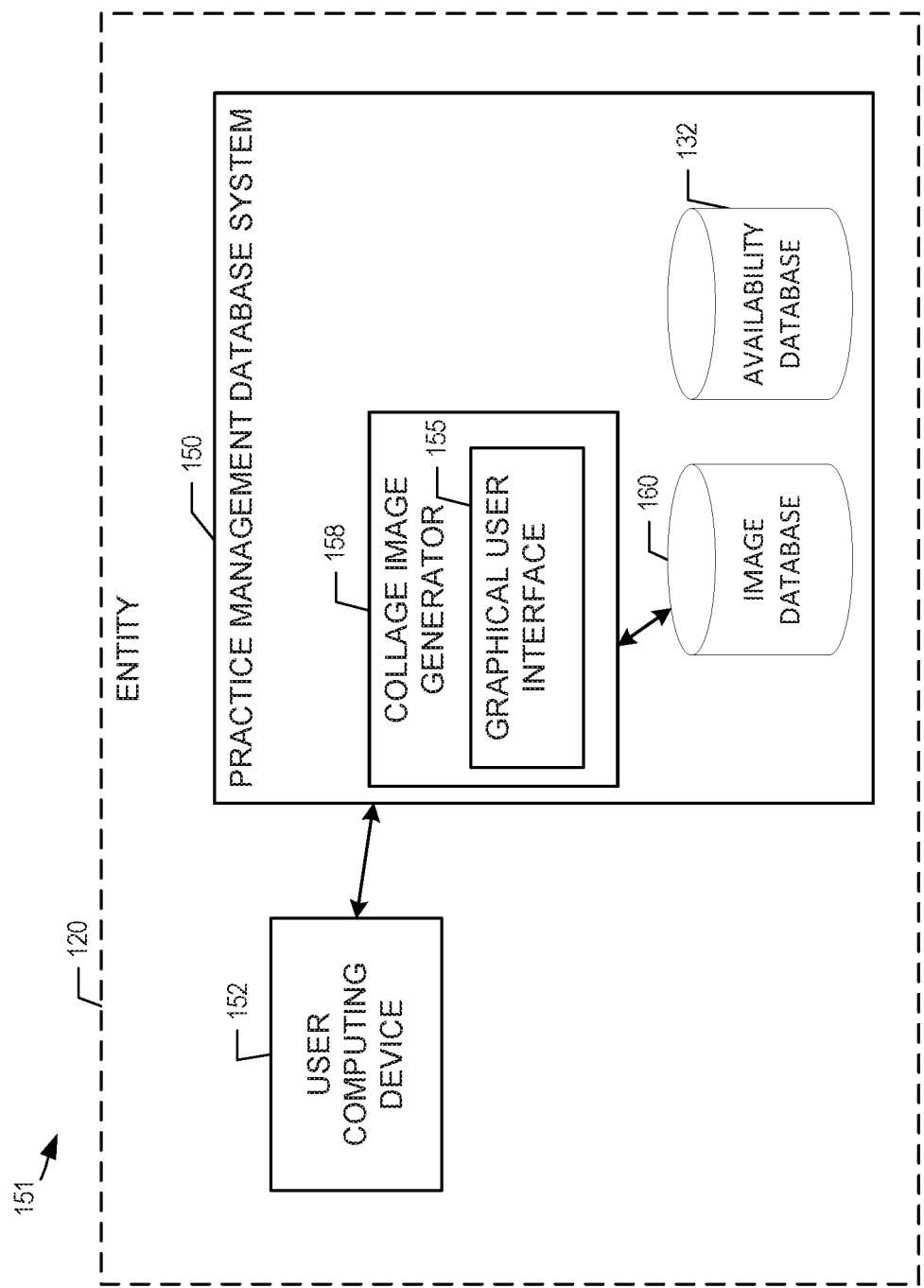
FIG. 1B illustrates a practice management database system, according to some embodiments of the present disclosure.

FIG. 1B illustrates a practice management database system 150, according to some embodiments of the present disclosure. In the embodiment of FIG. 1B, the computing environment 151 can include the entity 120. The entity 120 can include the user computing device 152 and the practice management database system 150. In some embodiments, the practice management database system 150 can include a practice management application that runs on the user computing device. In other embodiments, the practice management application can be implemented over a networked environment such as by presenting graphical user interfaces via a web browser application. Various communications between these devices are illustrated. For example, the user computing device 152 may transmit data, such as images, to the image database 160. The practice management database system 150 can include the image database 160, a collage image generator 158, and an availability database 132. The user computing device 102 may enable a user to interact with the graphical user interface 155 of the collage image generator 158. Accordingly, a user can create and store generated collage images in the image database 160. In some embodiments, the systems and/or devices of the practice management system 150 of FIG. 1B can be implemented in the same environment of the scheduling database system 100. For example, the availability database 132 of FIG. 1B can be the same as or similar to the availability database 132 of FIG. 1A.

Scheduling Embodiments

FIGS. 2A, 2B, 2C, 2D, 2E, 2F, 2G, 2H, and 2I illustrate example user interfaces of a scheduling database system, according to some embodiments of the present disclosure. In particular, FIGS. 2A, 2B, 2C, 2D, 2E, 2F, 2G, 2H, and 2I illustrate example user interfaces of the scheduling database system 100 described above with respect to FIG. 1A. In various embodiments, aspects of the user interfaces may be rearranged from what is shown and described below, and/or particular aspects may or may not be included. However, the embodiments described below in reference to FIGS. 2A, 2B, 2C, 2D, 2E, 2F, 2G, 2H, and 2I provide example user interfaces of a scheduling database system. The user interfaces of FIGS. 2A, 2B, 2C, 2D, 2E, 2F, 2G, 2H, and/or 2I such as the user interfaces 200, 230, 260, 266, 268, 272, 276, 278, and/or 286 may have similar user interface elements and/or capabilities. In some embodiments, the user interfaces described herein, such as the user interfaces 200, 230, 260, 266, 268, 272, 276, 278, and/or 286 of FIGS. 2A, 2B, 2C, 2D, 2E, 2F, 2G, 2H, and/or 2I can be presented within a web browser application. However, in other embodiments, the user interfaces described herein are not presented within a web browser application, such as by being presented within a mobile or desktop application.

Figure 2A:
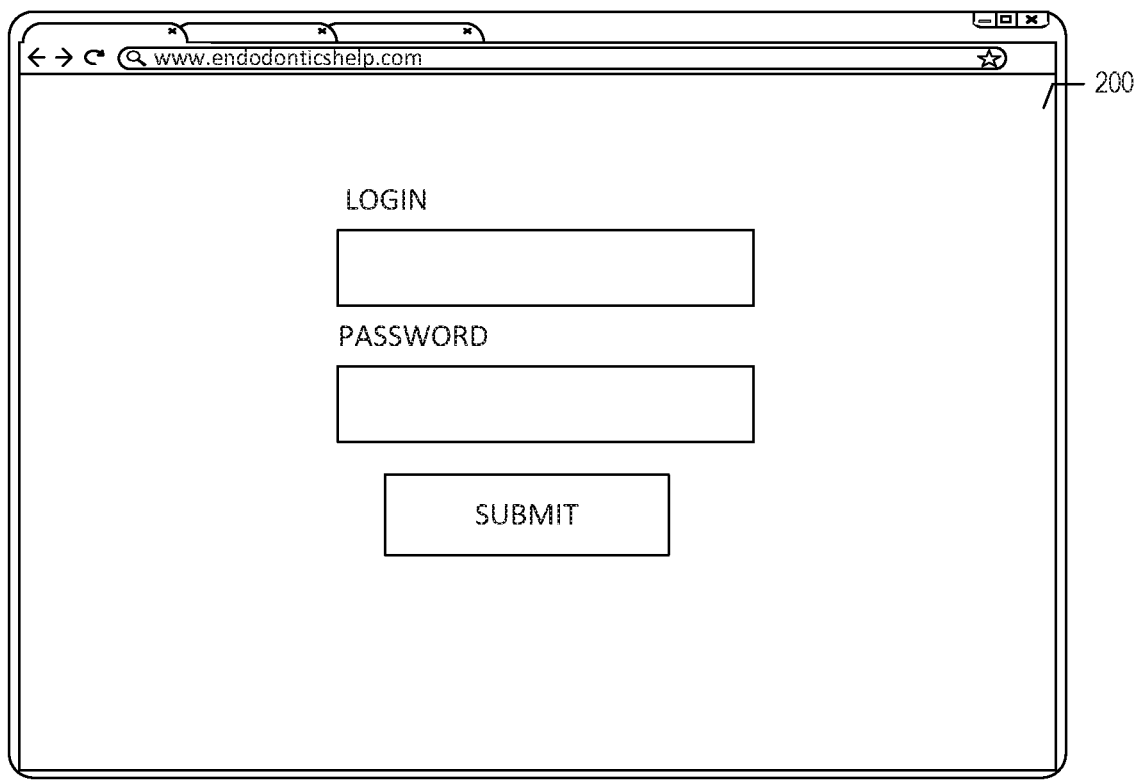

FIG. 2A illustrates an example login user interface 200 of the scheduling database system 100. The graphical user interface 200 can be used by user to schedule an appointment. The appointment can be on behalf of the user or on behalf of another. For example, a person can schedule their own appointment. As another example, a person visiting a general practitioner can have the general practitioner schedule their appointment. Thus, the login information that is provided by the user to the login user interface 200 can be personal login information or login information on behalf of an entity. The graphical user interface 200 can be an example scheduling input user interface.

Figure 2B:
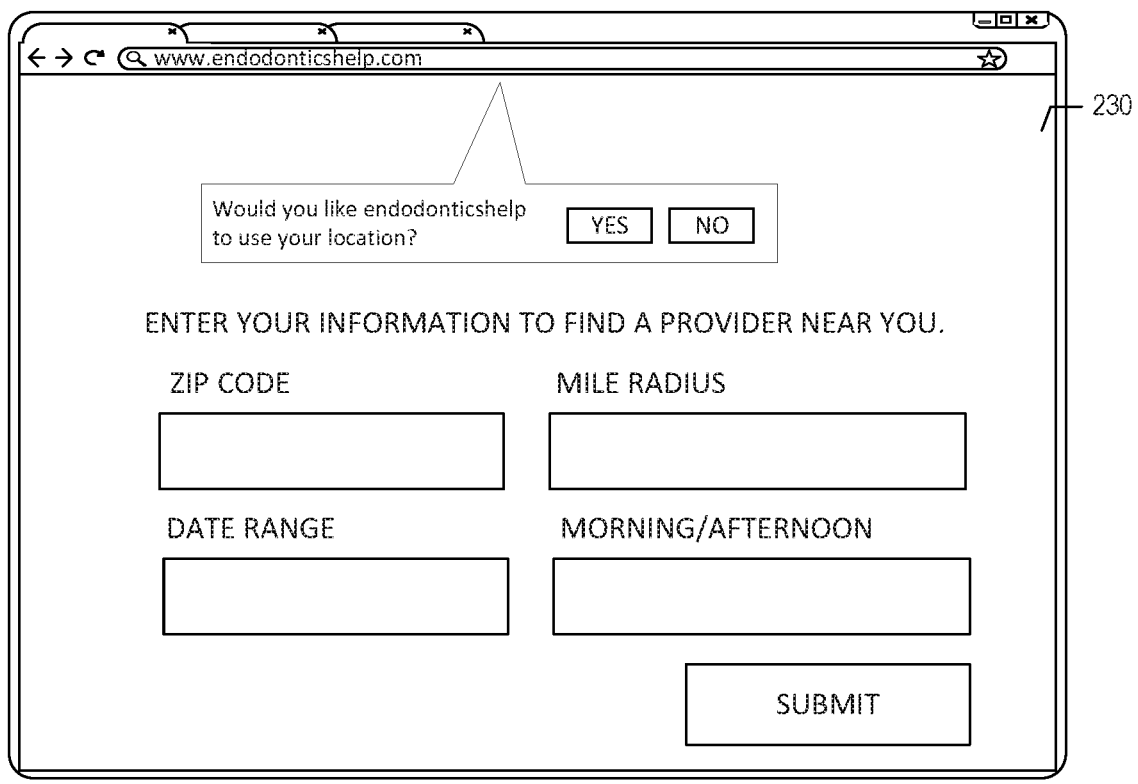

FIG. 2B illustrates an example preferences user interface 230 of the scheduling database system 100. The preferences user interface 230 includes user interface elements that enable a user to provide scheduling preference data. For example, a user can specify geographical parameter(s) (such as a zip code, distance radius, a current location, and/or other location data that can be used to identify entities near a location) and/or temporal parameters (such as a date range or a morning or afternoon preference). As described herein, the scheduling database system 100 can use the scheduling preference data to identify candidate appointment times. The graphical user interface 200 can be an example scheduling input user interface.

Figure 2C:
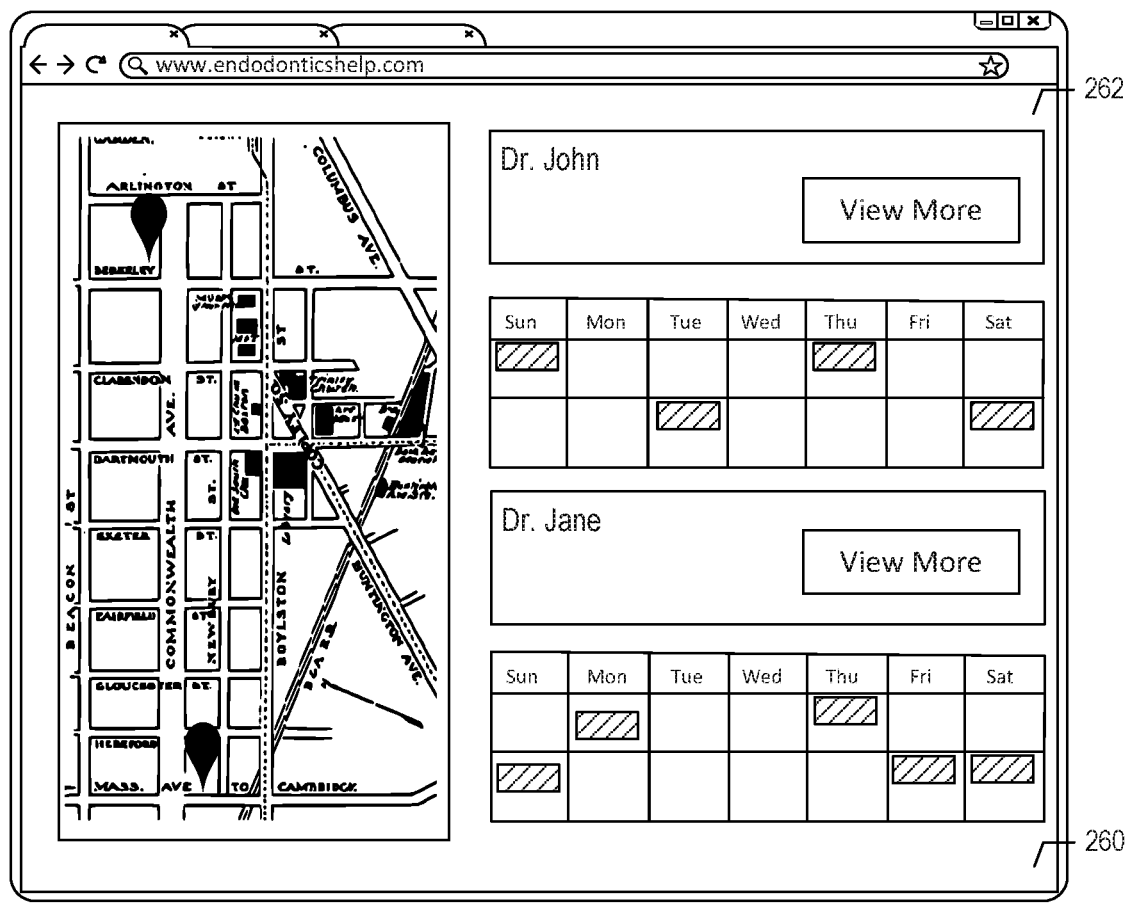

FIG. 2C illustrates an example scheduling user interface 260 of the scheduling database system 100. The scheduling user interface 260 can include scheduling information 262 that indicates candidate appointment openings that correspond to the scheduling preference data. Further, the scheduling database system 100 may present scheduling information 262 that has been customized. For example, if a general practitioner entity is scheduling an appointment for a person, the scheduling database system 100 may present scheduling availabilities for entities that have permissions for the particular general practitioner entity, as described herein. A user can then select an appointment slot within the scheduling user interface 260.

FIG. 2D illustrates an example login user interface 266 of the scheduling database system 100. The graphical user interface 266 of FIG. 2D can be similar to the graphical user interface 200 of FIG. 2A. As shown in FIG. 2D, the graphical user interface 266 can be accessed by a user schedule an appointment for a type of procedure, such as the GentleWave® procedure that uses multisonic ultracleaning technology to effectively clean and disinfect root canal systems while better preserving the tooth. As discussed above with respect to FIG. 2A, the appointment can be on behalf of the user or on behalf of another; a person can schedule their own appointment or a person visiting a general practitioner can have the general practitioner schedule their appointment. The user can login to view available appointments. In FIG. 2D, the login information that is provided by the user to the login user interface 266 can be personal login information or login information on behalf of an entity. A user can also create a new account via the login user interface 266.

Figure 2E:
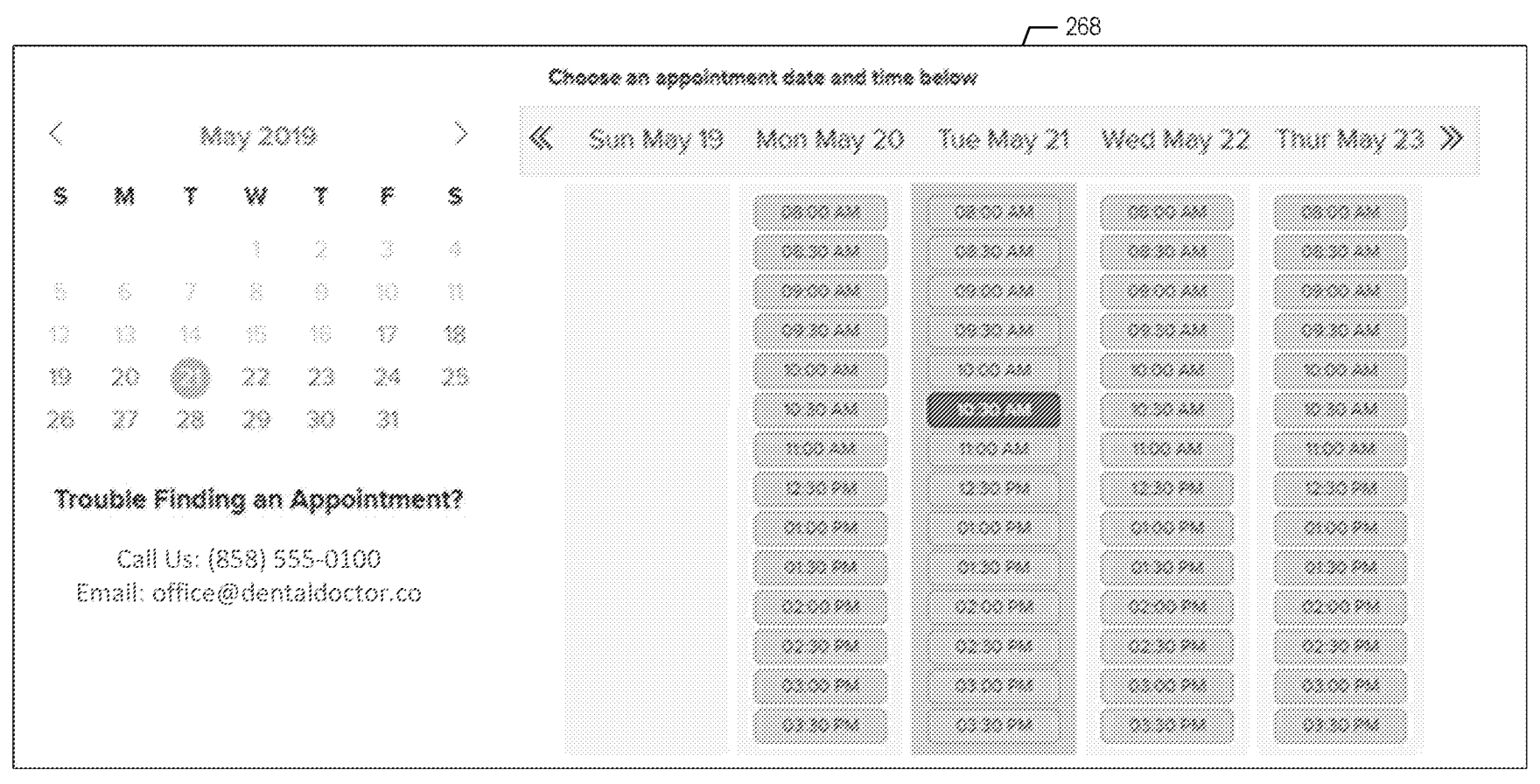

FIG. 2E illustrates an additional example scheduling user interface 268, of the scheduling database system 100. The graphical user interface 268 of FIG. 2E can be similar to the graphical user interface 260 of FIG. 2C. As shown in FIG. 2E, the scheduling user interface can present scheduling availabilities for an entity. A user can select an appointment slot within the scheduling user interface 268.

Figure 2F:

FIG. 2F illustrates an example appointment creation user interface 272 of the scheduling database system 100. As discussed above with respect to FIG. 2A, the appointment can be self-scheduled by the user or be made by the user on behalf of another. Thus, a person visiting an entity can have an administrator schedule or create their appointment with the appointment creation user interface 272. In some embodiments, a person can schedule or create their own appointment with the appointment creation user interface 272. As illustrated, the user can submit metadata, such as the tooth number input 274, which can be relevant to the scheduled appointment.

Figure 2G:
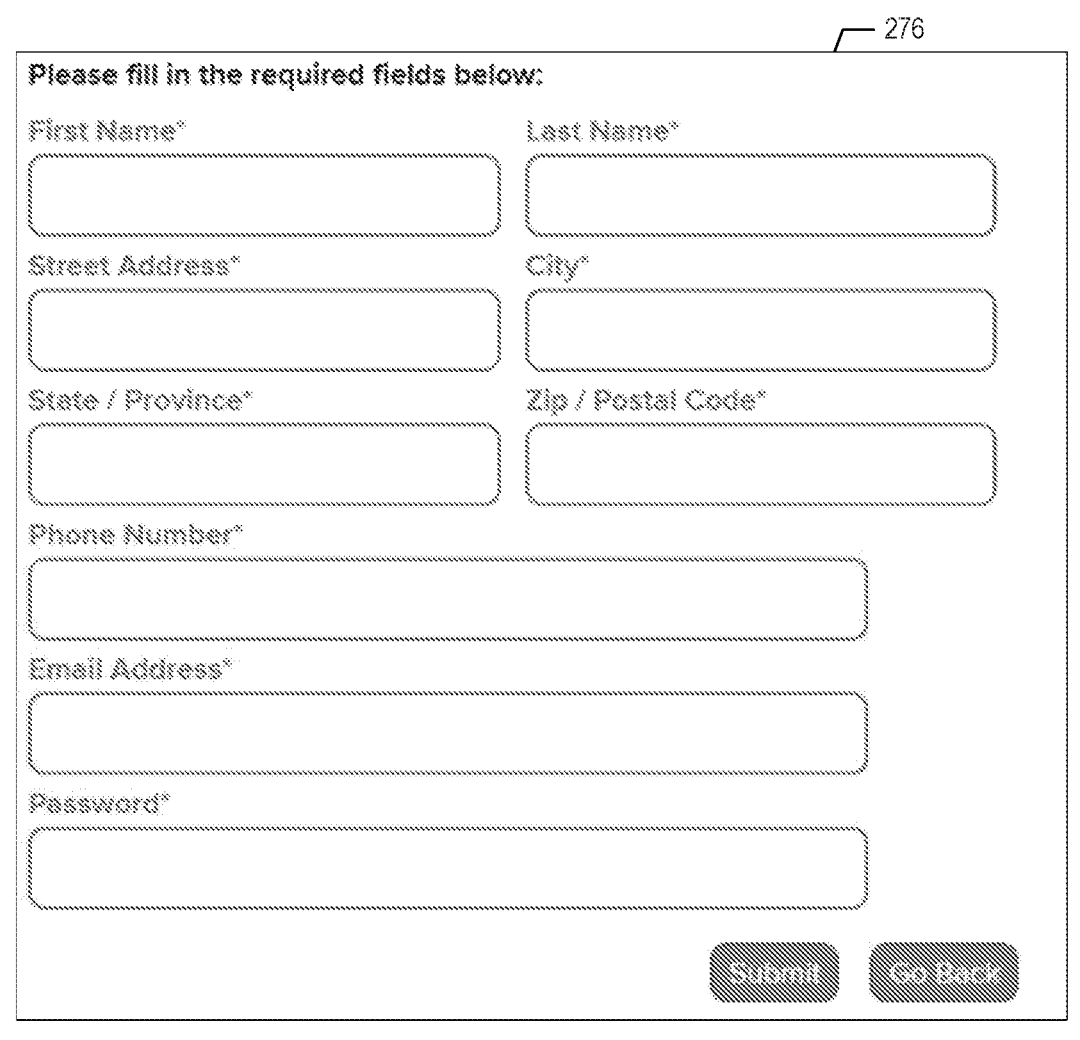

FIG. 2G illustrates an example account creation user interface 276 of the scheduling database system 100. The account creation user interface 276 can be used to create an account for a user or an entity, such as a referring entity account.

Figure 2H:
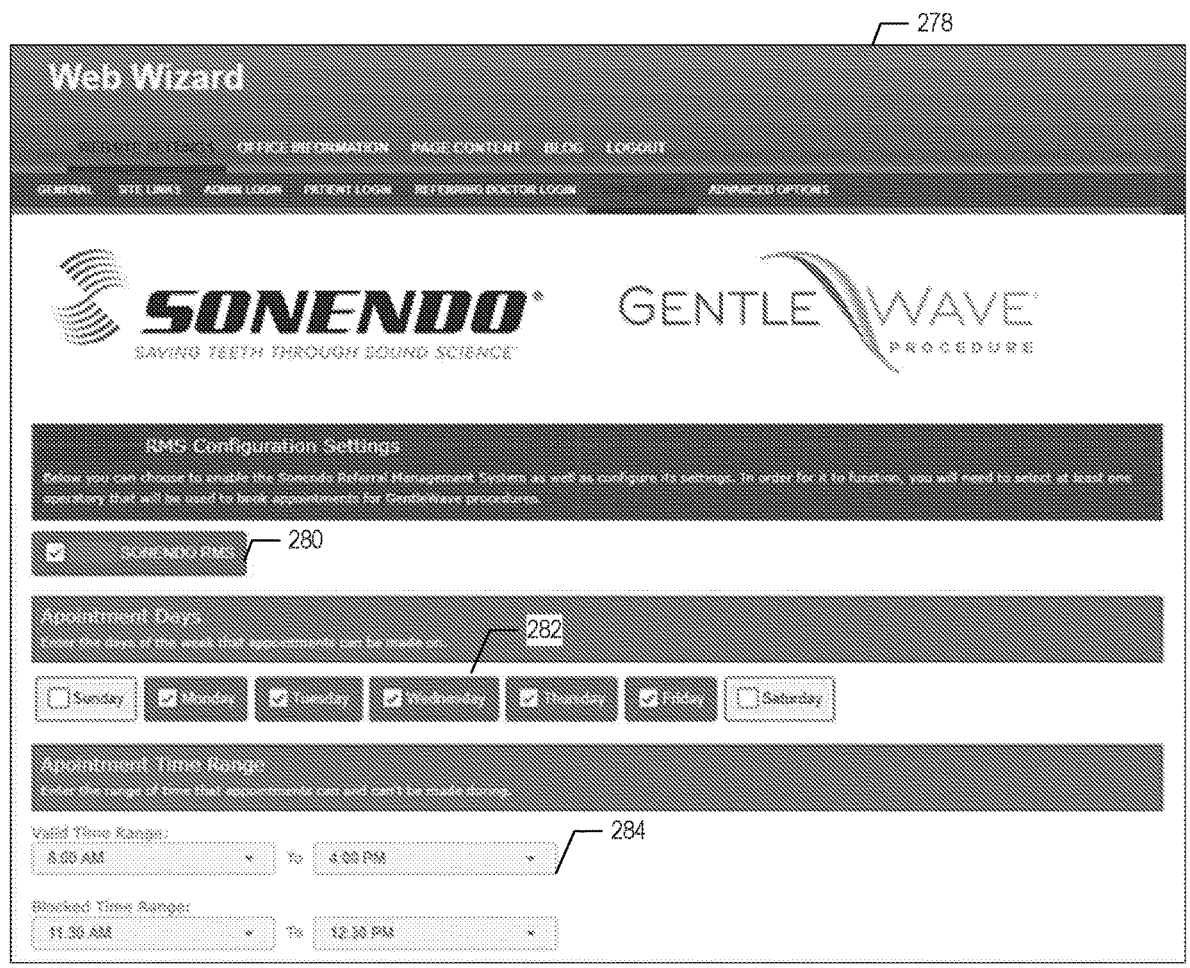
Figure 2I:
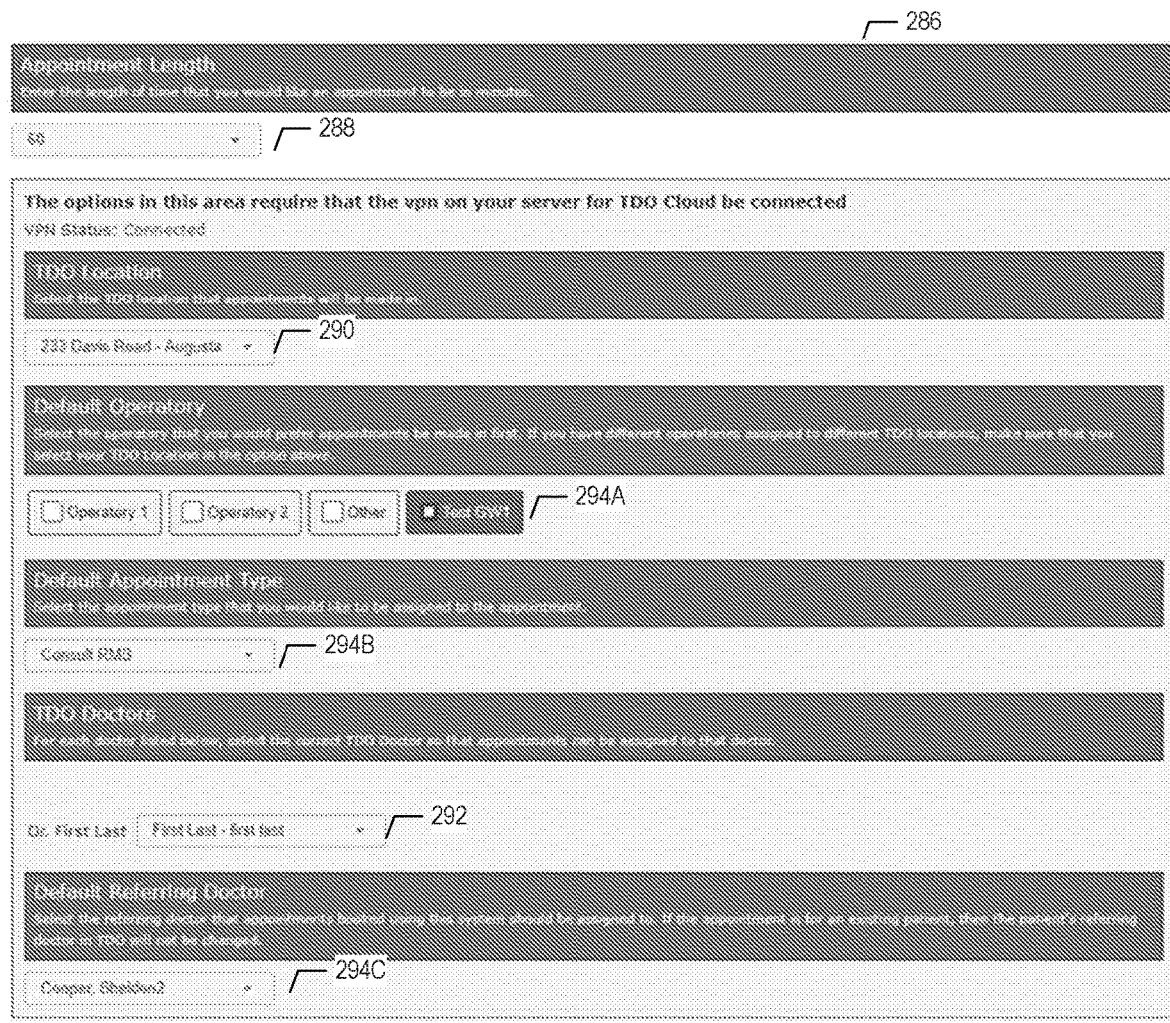

FIGS. 2H and 2I illustrate example entity configuration user interfaces 278, 286 of the scheduling database system 100. The entity configuration user interfaces 278, 286 can be used by an entity to specify referral-related configurations. In FIG. 2H, the first entity configuration user interface 278 can include a participation selector 280, an appointment days selector 282, and an appointment time range selector 284. A user can enable or disable an entity's participation with the participation selector 280. With the appointment days selector 282, a user can specify the days of the week that the entity is allowing for a potential referring entity to be able to schedule referral appointments. With the appointment time range selector 284, a user can specify time ranges that the entity is allowing for a potential referring entity to be able to schedule referral appointments.

In FIG. 2I, the second entity configuration user interface 286 can include an appointment length selector 288, a location selector 290, a doctor selector 292 and default configuration options 294A, 294B, 294C. With the appointment length selector 288, a user can specify a scheduled length of time for a referral appointment. With the appointment location selector 290, a user can specify an office location fix the referral appointment. With the doctor selector 292, a user can specify the doctor(s) that can be configured to receive referral appointments. With the default configuration options 294A, 294B, 294C, a user can specify various default options, such as a default workspace (also known as an operatory), a default appointment type, and a default referring doctor.

Figure 3:
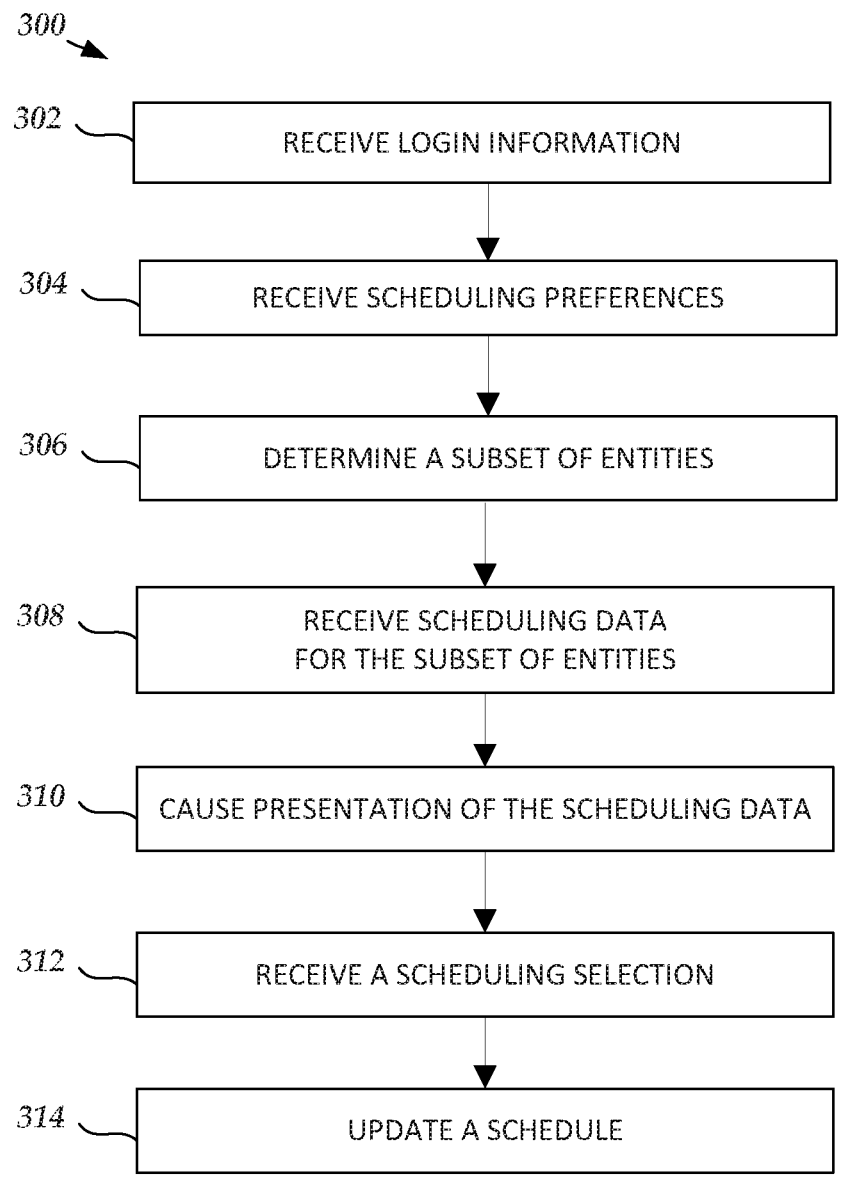
FIG. 3 is a flowchart of an example scheduling method, according to some embodiments of the present disclosure.

FIG. 3 is a flowchart of an example scheduling method 300, according to some embodiments of the present disclosure. Although the method 300 is described in conjunction with the systems of FIG. 1A, any system configured to perform the method, in any order, is within the scope of this disclosure. The method 300 may be performed by the various components of the scheduling database system 100 of FIG. 1A as discussed herein, including the scheduling server 108 and/or the scheduling service 106. Depending on the embodiment, the method 300 may include fewer or additional blocks and/or the blocks may be performed in an order different than is illustrated.

Beginning at block 302, login information can be received. For example, the scheduling server 108 can receive login information. The scheduling server 108 can present a login user interface, such as the user interfaces 200, 266 that are described in further detail above with respect to FIGS. 2A, 2D. A user can login personally (such as individuals scheduling appointment for themselves) or the user can login on behalf of an entity (such as an administrator at a general practitioner scheduling an appointment for an individual). The scheduling server 108 can determine a profile from the login information, such as an individual profile or an entity profile. As described herein, a profile can be used to determine scheduling search results, such as by determining authorized entities for the profile.

At block 304, scheduling preferences can be received. For example, the scheduling server 108 can receive scheduling preferences. The scheduling server 108 can present a preferences user interface, such as the user interface 230 that is described in further detail above with respect to FIG. 2B. Example scheduling preferences can include geographical parameters (such as a zip code, distance radius, a current location, and/or other location data) and/or temporal parameters (such as a date range or a morning or afternoon preference). As described herein, the scheduling preferences can be used to determine a subset of entities and/or scheduling search results.

At block 306, a subset of entities can be determined. For example, the scheduling database system 100 (such as the scheduling server 108 and/or the scheduling service 106) can determine a subset of entities according to the scheduling search preferences. If the scheduling search preferences include geographical and/or temporal parameters, the scheduling database system 100 can identify those entities that satisfy those parameters, such as being within a geographical area and/or that have appointments within the temporal parameters. In some embodiments, the scheduling database system 100 can query each of the entities for their appointment availability, which can occur over a virtual private network. Additionally or alternatively, the scheduling database system 100 can maintain a central scheduling database, such as the database 110, which can be synchronized with the scheduling databases at each of the entities. Querying a central scheduling database for multiple entities can advantageously have better performance than querying multiple individual scheduling databases. The scheduling service 106 can synchronize between the central scheduling database 110 and the entity scheduling databases periodically, which is described in further detail below with respect to FIG. 5.

The scheduling database system 100 can include additional logic to determine authorizations (or a lack thereof) for a profile with respect to some entities. Thus, the scheduling database system 100 can determine that a first profile lacks authorization for a particular entity and thus can exclude the particular entity. Some entities may specify in configuration data that referrals should only be received from general practitioners (as opposed to individuals' scheduling appointments directly). Thus, if the profile is not for a general practitioner, such as an individual profile, then the scheduling database system 100 can exclude such entities from the subset of entities. The scheduling database system 100 determining that a first profile lacks authorization for a particular entity can include determining that the first profile corresponds to a profile for a person.

Conversely, the scheduling database system 100 can determine that a first profile has authorization for a particular entity (such as the profile being for a general practitioner), and the determined subset of entities can include the particular entity. The scheduling database system 100 can add the particular entity to the subset of entities. The scheduling database system 100 determining that a second profile has authorization for a particular entity can include determining that the second profile corresponds to a general practitioner. Additionally or alternatively, the scheduling database system 100 determining that a second profile has authorization for a particular entity can include determining that the second profile corresponds to a preferred referrer for the first entity. The first entity can submit referral preferences that identify which other entities (that can correspond to particular general practitioners, for example) have authorization rights, which can further indicate that other entities lack authorization rights. The determination of whether an entity is a preferred referrer can be based on analytics, such as analytics indicating the top three referring entities for a specialist. The scheduling database system 100 can determine analytics by calculating a first number of referrals from a profile to a first entity and a second number of referrals from another profile to the first entity. The scheduling database system 100 can determine that the first number of referrals is greater than the second number of referrals. Thus, if a particular entity or profile has a higher number of referrals relative to other entities or referrals (such as a top three referrer), the scheduling database system 100 can designate the particular entity or profile as a preferred referrer for the entity that receives the referral. The scheduling database system 100 can therefore include rules to dynamically determine a subset of entities.

Participation by entities in the referral network and/or the presentation of scheduling information can also be based on other criteria. The search results in some cases can be limited to entities with specific equipment and/or that offer certain procedures. For example, the provided scheduling information can be limited to entities that offer ultrasonic root canal cleaning procedures, such as procedures offered by the GentleWave® System offered by Sonendo, Inc. Thus, users searching for particular types of procedures can receive scheduling search results for entities that offer those types of procedures.

In some embodiments, part of the scheduling process for individual users can include completing a self-diagnosis user interface. The scheduling server 108 can present a self-diagnosis user interface, such as by presenting questions to a user related to the type of appointment that the user would like to schedule. The input from the self-diagnosis user interface can be used by the scheduling database system 100 as a pre-filter. For example, an individual user may only be able to view scheduling information after completing the self-diagnosis user interface to prevent the unnecessary appointments described herein. In some embodiments, certain entities may employ the self-diagnosis user interface as a prerequisite before the entity will allow an individual user to schedule an appointment from that entity.

At block 308, scheduling data can be received. For example, the scheduling database system 100 (such as the scheduling server 108 and/or the scheduling service 106) can retrieve scheduling data for the subset of entities. The scheduling database system 100 can retrieve appointment slots for each entity of the subset of entities. The appointment slots can be available or not available. In some embodiments, as described above, the scheduling database system 100 can maintain a central scheduling database for appointment slots for multiple entities, which can be periodically updated and/or synchronized with the scheduling databases for each entity. Allowing each entity to specify appointment slots can enable entities greater control over their schedules to only have select days or portions of days for scheduling through the scheduling database system 100. In some embodiments, an entity can specify scheduling availability in one or more user interfaces, such as the user interfaces 278 and 286 that are described in further detail above with respect to FIGS. 2H and 2I.

At block 310, the scheduling data can be presented. For example, the scheduling server 108 can present scheduling data (such as appointment slots) in a scheduling user interface. Scheduling user interfaces 260, 268 are described in further detail above with respect to FIGS. 2C, 2E, The scheduling user interface can present appointment slots for the respective subset of entities that correspond to the scheduling preferences. Further, as described herein, the scheduling user interface can present appointment slots for entities that have been authorized for presentation for the particular profile, which can exclude unauthorized entities for the profile.

At block 312, a scheduling selection can be received. For example, the scheduling server 108 can receive a scheduling selection for an entity via a scheduling user interface, such as the user interfaces 260, 268 that are described in further detail above with respect to FIGS. 2C, 2E. The scheduling selection can include an appointment slot for an entity. As described herein, the scheduling user interface can present appointment slots for entities that have been authorized for presentation for the particular profile, which can exclude unauthorized entities for the profile. Thus, a scheduling selection may be received for authorized entities and not for unauthorized entities. A scheduling selection may also include changing and/or cancelling an appointment. As described herein, the appointment for the entity can correspond to a special practitioner such as an endodontist.

At block 314, a schedule may be updated according to the scheduling selection. For example, the scheduling database system 100 (such as the scheduling server 108 and/or the scheduling service 106) can update an appointment entry (by adding, deleting, or changing an appointment entry) in a scheduling database. In some embodiments, as described above, the scheduling database system 100 can maintain a central scheduling database, which can be updated according to the scheduling selection. The updated appointment slot can then be propagated to a respective entity's scheduling database. The updated appointment slot can appear in the entity's practice management database system, which can be presented in a user interface that is described in further detail below with respect to FIG. 6.

In some embodiments, the scheduling service 106 and/or the scheduling server 108 can attempt to connect to an entity to propagate a scheduling entry in near time. Thus, if a connection to the entity 120 from the scheduling database system 100 can be made, the scheduling service 106 can update the entity's database 132 in near time. However, as described herein, an attempted connection may have a fail status due to network issues and/or a VPN connection being unavailable. If a connection is unavailable, the updated scheduling data can be propagated via a synchronization process. In the scheduling database system 100, a scheduling entry in the central scheduling database 110 can include a synchronization status that marks the scheduling entry for future propagation. Additionally or alternatively, a synchronization status can be set in the entities' database(s) 132 can be used to mark an entry for synchronization purposes. Additional details regarding synchronizing scheduling data between the scheduling database 110 and the entities' databases are described in further detail below with respect to FIG. 5.

Figure 4:
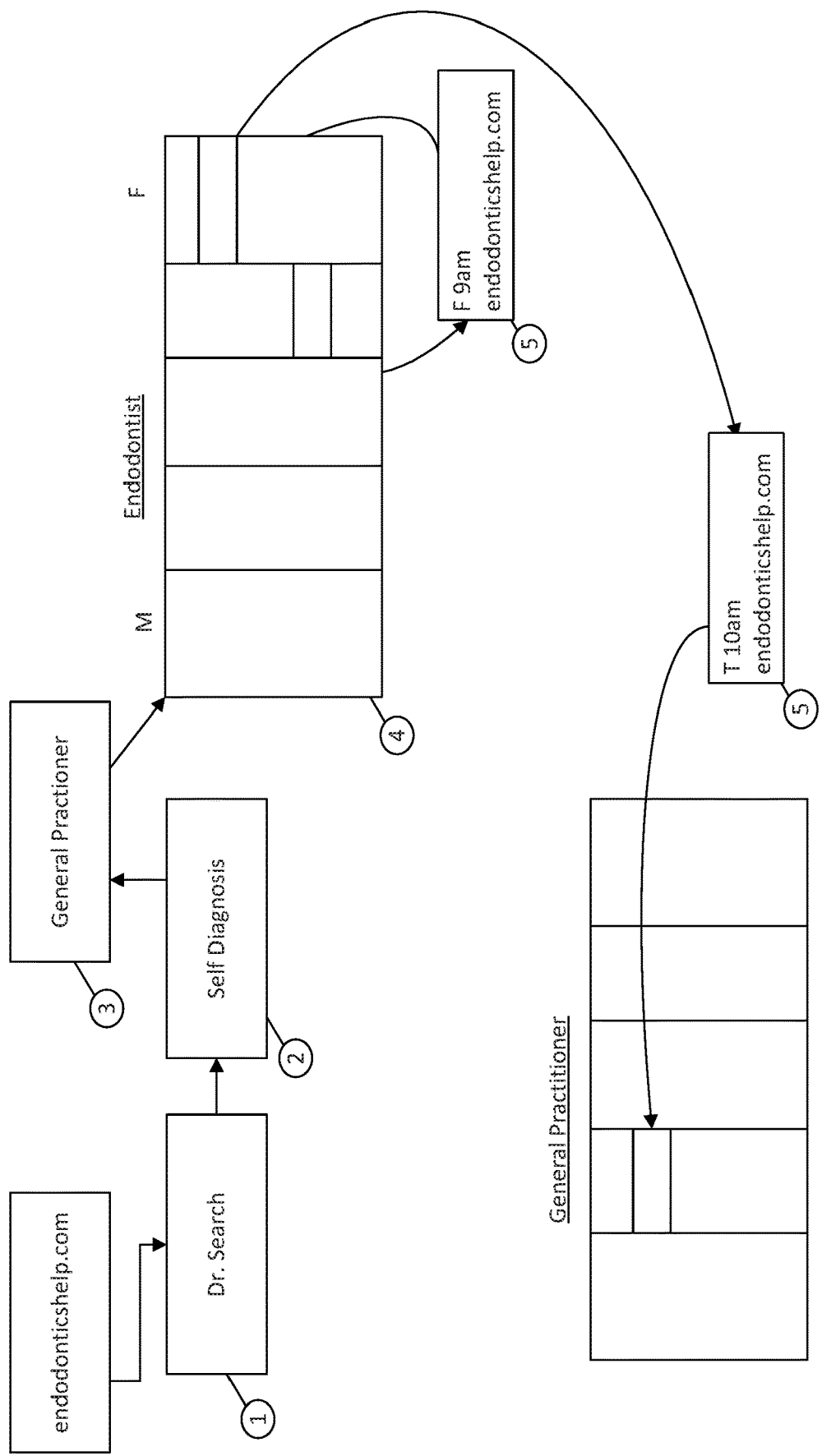
FIG. 4 depicts an example scheduling workflow, according to some embodiments of the present disclosure.

In FIG. 4, an example scheduling workflow is depicted. An example workflow can proceed in the following manner: at (1) a user can visit a website and search for a dental specialist doctor (such as an endodontist); at (2) a patient can perform a self-diagnosis via the website; at (3) a patient can optionally be referred to a general practitioner dentist; at (4) the patient can schedule their appointment online; at (5) the patient can be provided with a card before, during, or after their general practitioner/specialist appointment that can include login/website information to reschedule an appointment at any time; throughout the process patient information/files can be transmitted between practicing offices; and/or since the patient has provided their information already, the normal paperwork process of visiting a new office can be reduced to simply logging in with their credential information.

For example, Person A has severe toothache pain and Person A believes they may need a root canal. Person A visits endodonticshelp.com, and they can search for endodontists in the nearby area that have schedule availabilities in the next few days. Through endodonticshelp.com, Person A fills out a questionnaire that results in a recommendation that Person A visit a general practitioner or an endodontist. Person A schedules their appointment and can print out a card that has their appointment schedule along with details to reschedule their appointment, if necessary. Person A can securely provide personal/health information via endodonticshelp.com. Person A visits the scheduled endodontist, and can check in by providing their login credentials from endodonticshelp.com. At the conclusion of the root canal, Person A is provided with a follow-up appointment card for a general practitioner. Since the endodontist and the general practitioner's offices are interlinked via an office management system, Person A's files from the endodontist can be seamlessly transmitted to the general practitioner. Person A attends the follow up appointment at the general practitioner, and, again, can check in by providing their login credentials from endodonticshelp.com. The general practitioner can access the files provided by the endodontist and vice versa.

In some embodiments, each entity can have referral preferences. Respective entities can selectively join or be removed from the scheduling network. For example, the scheduling database system 100 can receive referral configuration data from participants. The scheduling database system 100 can update the referral network according to the configuration data, such as by removing or adding entities to the network. The scheduling database system 100 can then permission participant referrals based on the referral network. Using the scheduling database system 100, an entity can specify their working/availability hours, which can be reflected in their shared scheduling information.

In some embodiments, advantages of the approaches described herein can include allowing a user to quickly schedule appointments, follow-up appointments, and to make changes to those appointments. Entities can securely communicate with each other, such as by using the practice management solutions, the normal paperwork process of visiting a new entity can be reduced greatly be using credential information. Further, any entity using the scheduling database system 100 can have greater control over their working hours with respect to referrals.

In some embodiments, the scheduling database system 100 can provide analytics to users. As described herein, the analytics can include statistical measures relating to referrals for each entity. Additional statistical data can include calculations related to a number of procedures completed by an entity. The statistical measures can be provided to individual users and/or entities. The statistical measures can also be used to rank results presented to users. Such as by presenting entities in search results according to a number of procedures completed and/or based on reviews.

Figure 5:
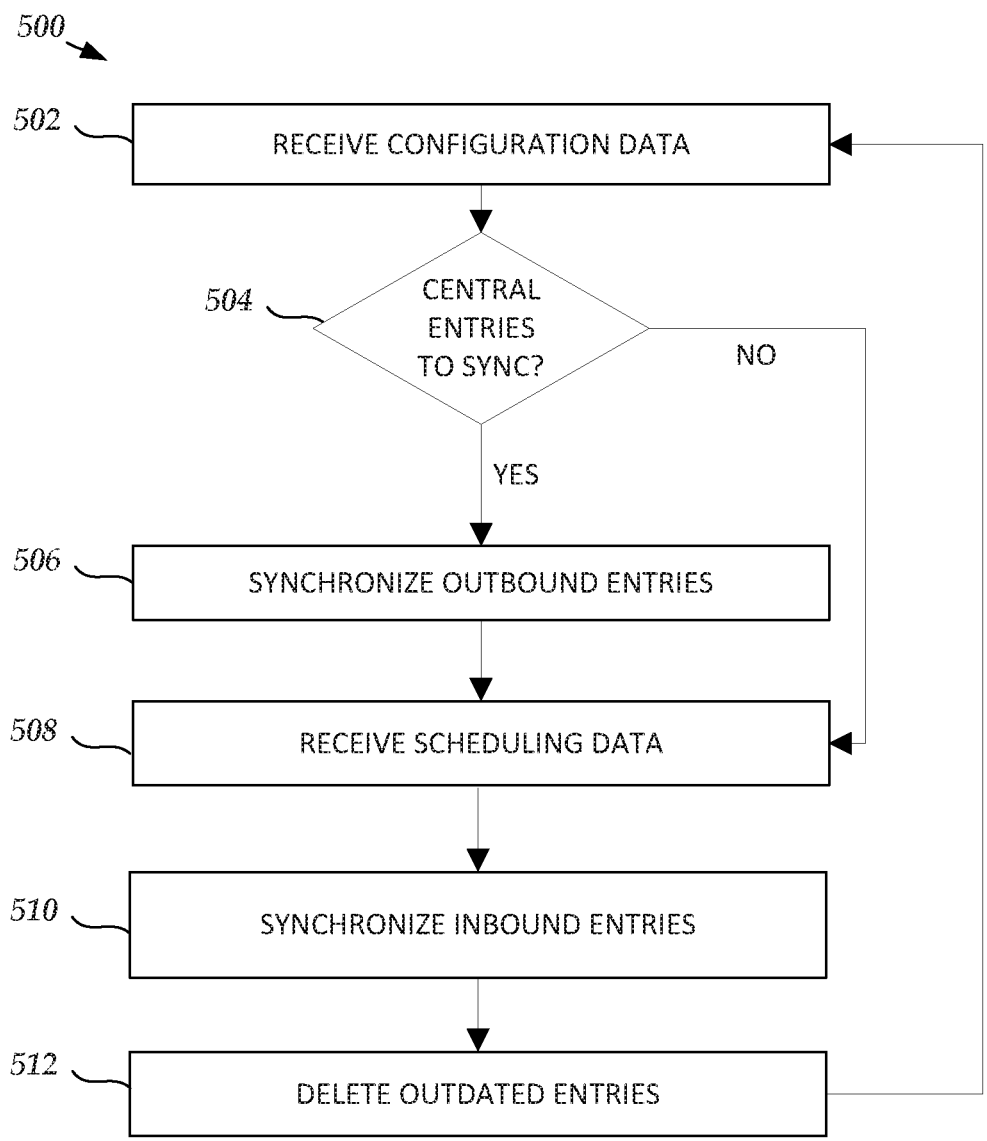
FIG. 5 is a flowchart of an example synchronization method, according to some embodiments of the present disclosure.

FIG. 5 is a flowchart of an example synchronization method 500, according to some embodiments of the present disclosure. Although the method 500 is described in conjunction with the systems of FIG. 1A, any system configured to perform the method, in any order, is within the scope of this disclosure. The method 500 may be performed by the various components of the scheduling database system 100 of FIG. 1A as discussed herein, including the scheduling service 106. Depending on the embodiment, the method 500 may include fewer or additional blocks and/or the blocks may be performed in an order different than is illustrated.

The method 500 may be executed by the scheduling service 106 to synchronize scheduling entries between the central scheduling database 110 and the one or more entities 120. The scheduling service 106 can be configured to run asynchronously to synchronize the entries. The scheduling service 106 can synchronize entries on a periodic basis, such as running every few minutes, hours, etc.

Beginning at block 502, configuration data can be received. In particular, the scheduling service 106 can receive configuration data, such as, but not limited to, for entities that are configured to use the scheduling database system's 100 scheduling features. As described herein, entities can selectively opt-in or out of the referral network.

As described above with respect to block 314 of FIG. 3, a scheduling entry can include a field with a synchronization status. The one or more synchronization statuses can be an enumerated type. Example synchronization statuses can include: "Need to Sync to Entity," "Synced," and "Need to Sync from Entity." The "Need to Sync to Entity" synchronization status can mark a scheduling entry for future propagation to an entity. As described herein, the web server 108 can fail to propagate a scheduling entry in near time, and, therefore, a field in the scheduling entry can be set to the "Need to Sync to Entity" synchronization status that marks the entry for future propagation. The "Synced" synchronization status can indicate a synchronization complete status. The "Need to Sync from Entity" synchronization statuses can indicate that an entry should receive a synchronization check from an entity to the central scheduling database 110. Additional details regarding the synchronization statuses are described in further detail below with respect to the method 500.

At block 504, it is determined whether entries from the central scheduling database 110 should be synchronized to an entity. In particular, the scheduling service 106 can determine whether this is an entry that should be synchronized from the central scheduling database 110 to an entity, such as in the case where a near-time propagation fails. As described herein, each of the scheduling entries can have a field that can be used to set a synchronization status. The scheduling service 106 can determine to synchronize a scheduling entry based at least in part on the synchronization status of the scheduling entry. For example, the scheduling service 106 can check whether any scheduling entries have a "Need to Sync to Entity" synchronization status. In particular, the scheduling service 106 can check whether any entries should be propagated for the entities that are configured with the scheduling database system 100 as specified by the previous block 502. If there are no entries that should be synchronized from the central scheduling database 110 to the one or more entities 120, then the scheduling service 106 can proceed to block 508.

At block 506, if it has been determined to synchronize an entry from the central scheduling database 110 to the one or more entities 120, a scheduling entry can be synchronized. The scheduling service 106 can cause propagation of a scheduling entry from the central scheduling database 110 to the database 132 of an entity 120. In particular, the scheduling service 106 can cause a second scheduling entry to be stored or updated in a database 132 of an entity where the second scheduling entry can correspond to a first scheduling entry in the central scheduling database 110. The scheduling service 106 can cause propagation of scheduling entries in the central scheduling database 110 that have a "Need to Sync to Entity" synchronization status.

At block 508, scheduling data can be received from the one or more entities 120. The block 508 for receiving scheduling data can be similar to the block 308 described above with respect to FIG. 3, In particular, the scheduling service 106 can receive scheduling data for a period of time, such as 30 or 90 days in advance of a current day or time. The scheduling data can include availability configuration data from an entity, which is described in further detail above with respect to FIGS. 2H and 2I. The scheduling service 106 can store, in the central scheduling database 110, additional scheduling data corresponding to the received scheduling data. An entity can update their scheduling data, such as preferences and/or availability times, and the scheduling service 106 can receive the updated scheduling data. The scheduling data can also include scheduling entries or appointments from an entity, such as the scheduling entries in the entity's database 110. As described herein, the scheduling database system 100 can connect with the one or more entities 120 over a secure protocol, such as a VPN.

At block 510, inbound scheduling entries can be synchronized. In particular, the scheduling service 106 can compare the received schedules from the entity 120 to the schedules in the central scheduling database 110. The scheduling service 106 can store new scheduling entries in the central scheduling database 110. The scheduling service 106 can also set a field in a scheduling entry in the central scheduling database 110 to a synchronization status that marks a scheduling entry for a synchronization check from an entity to the central scheduling database 110. In other words, the scheduling service 106 can set existing scheduling entries in the central scheduling database 110 to the "Need to Sync from Entity" synchronization status. The scheduling service 106 can determine that a scheduling entry in the central scheduling database 110 has a corresponding entry in the database 132 of an entity 120. In other words, each of the entries with the "Need to Sync from Entity" synchronization status can be compared against corresponding entries (which may or may not exist) in the database 132 of an entity 120. The scheduling service 106 can update the field in the scheduling entry from the "Need to Sync from Entity" synchronization status to another synchronization status indicating a synchronization complete status. In other words, if the scheduling entry in the central scheduling database 110 has a corresponding entry in the database 132, then the scheduling service can set the synchronization status of the scheduling entry to "Synced."

At block 512, outdated scheduling entries can be deleted. In particular, the scheduling service 106 can delete outdated scheduling entries in the central scheduling database 110. As mentioned above at the previous block 510, multiple entries can be set to a synchronization status that marks each of the entries for a synchronization check from an entity to the central scheduling database 110, which can be referred to herein as the "Need to Sync from Entity" synchronization status. Of those entries, those that have a corresponding entry are set to "Synced." After block 510, the scheduling service 106 can determine to preserve e.g., not delete) a scheduling entry based at least in part on the field being set to the "Synced" synchronization status. Conversely, any remaining entries with a "Need to Sync from Entity" synchronization status can be deemed to be outdated because they do not have a corresponding entry in the entity database 132. The outdated entries can be deleted in the central scheduling database 110. For example, an update could occur at the entity 120, which removes the entity's scheduling entry and the removal can in effect be propagated to the central scheduling database 110.

As shown, the method 500 can return to the start block 502 after the end block 512 because the method 500 can run as a background synchronization process between the scheduling database system 100 and the entities 120.

In some embodiments, the scheduling database system 100 and/or the entities 120 allow double bookings. Accordingly, having asynchronous and/or separate processes making appointments for the same time slots can be handled by the scheduling database system 100 and/or the entities 120. For example, at the entity 120, an administrator can review any double bookings and can reschedule or cancel as appropriate.

Collage and Practice Management Embodiments

In a dental context, dentists often give presentations about interesting cases or share those cases with other dentists. In such cases, dentists might typically share images from those cases. Dentists can use word processing programs, image editing programs, or presentation programs to assemble images for presentation or sharing purposes. Using the programs, dentists can manually arrange images for presentation or sharing.

FIGS. 6, 7, 8A, 8B, 8C, 8D, 8E, 8F, 8G, 8H, 8I, and 8J illustrate example user interfaces of a practice management database system, according to some embodiments of the present disclosure. In particular, 6, 7, 8A, 8B, 8C, 8D, 8E, 8F, 8G, 8H, 8I, and 8J illustrate example user interfaces of the practice management database system 150 described above with respect to FIG. 1B. In various embodiments, aspects of the user interfaces may be rearranged from what is shown and described below, and/or particular aspects may or may not be included. In some embodiments, the user interfaces described herein, such as the user interfaces of 6, 7, 8A, SB, 8C, 8D, 8E, 8F, SG, 8H, 8I, and 8J can be presented within a web browser application. However, in other embodiments, the user interfaces described herein are not presented within a web browser application, such as by being presented within a mobile or desktop application.

Figure 6:
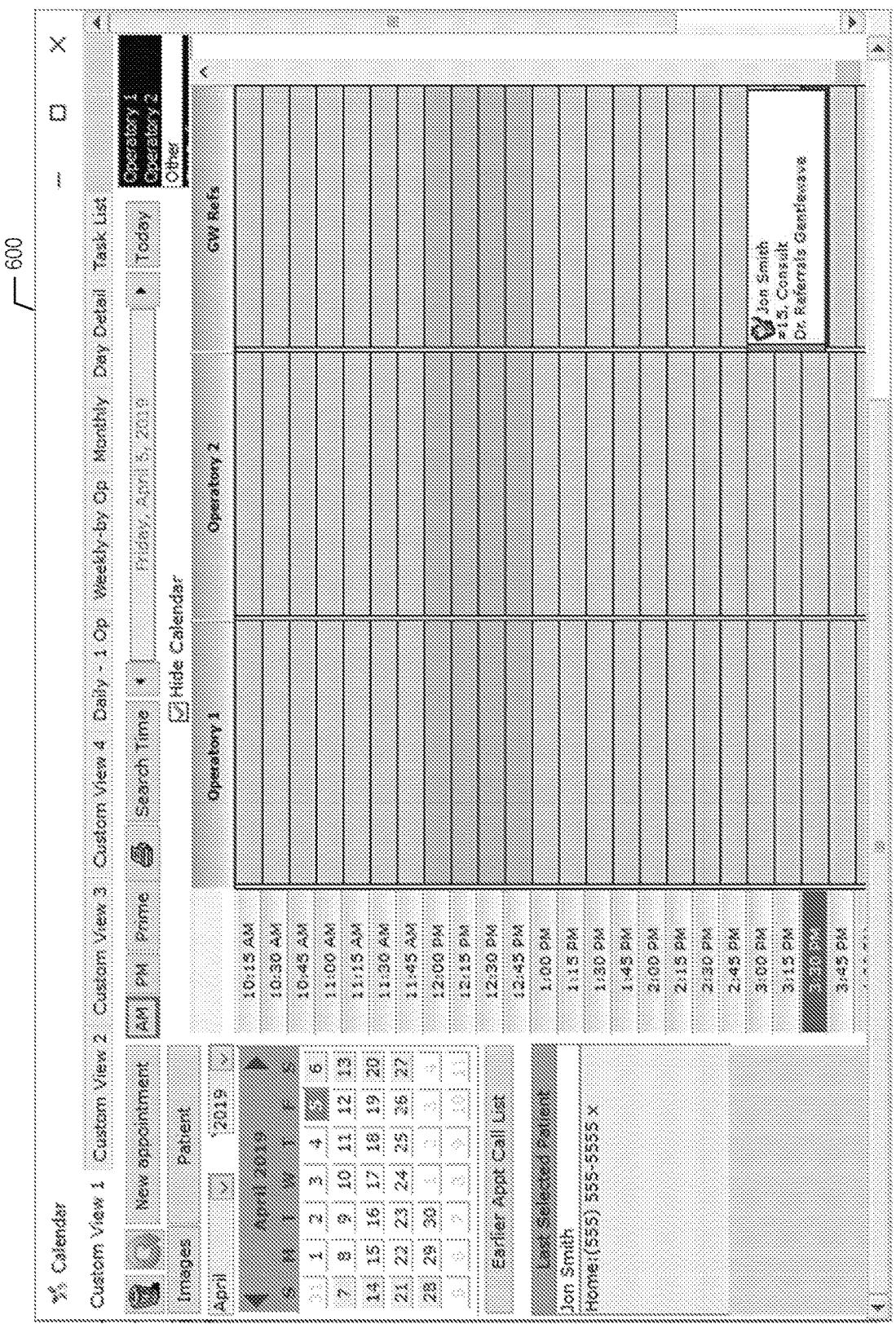
FIGS. 6, 7, 8A, 8B, 8C, 8D, 8E, 8F, 8G, 8H, 8I, and 8J depicts an example graphical user interfaces of a practice management database system, according to some embodiments of the present disclosure.

In FIG. 6, a graphical user interface 600 is presented for a practice management application. As shown, the graphical user interface 600 can enable a user to view a scheduling entry. The scheduling entry can be received from the scheduling database system 100 (e.g., an appointment is booked through a user interface of the scheduling database system 100) and/or the scheduling entry can be propagated to the scheduling database system 100 (e.g., an appointment is booked through a user interface of the practice management application).

Figure 7:
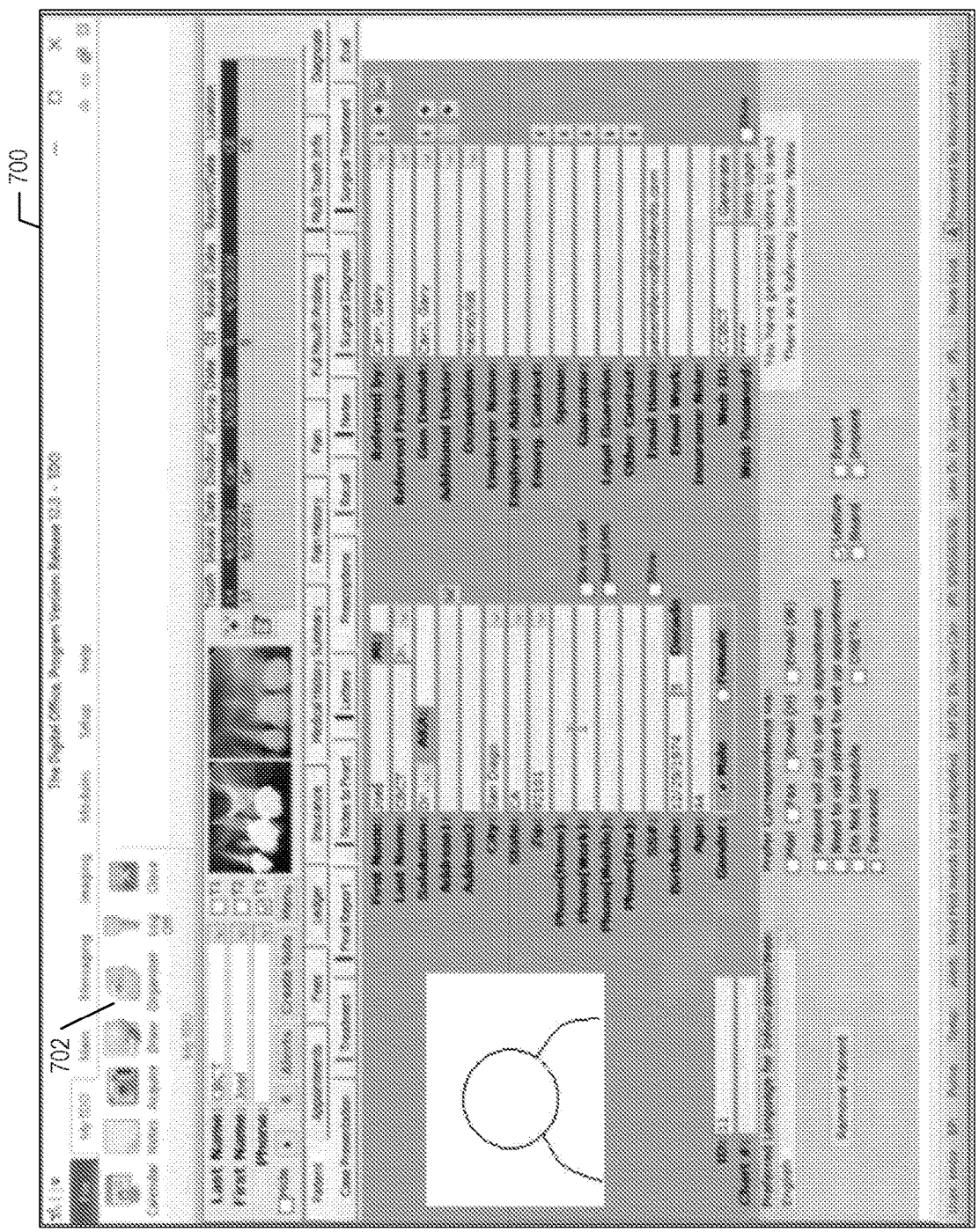

In FIG. 7, a graphical user interface 700 is presented for a practice management application. As shown, the graphical user interface 700 can enable a user to view information regarding a person, such as a patient, which can include, but is not limited to, demographic details, historical data, and/or image data. The practice management application can include features for charting, scheduling, financials, or reports for an entity. The practice management application can support images from different digital imaging technologies, such as, but not limited to, cone-beam CT imaging, digital radiography, digital photography, hi-definition video capture, or and dental microscopy. The graphical user interface 700 can include a user interface element 702 that opens an application to organize practice management files.

Figure 8A:
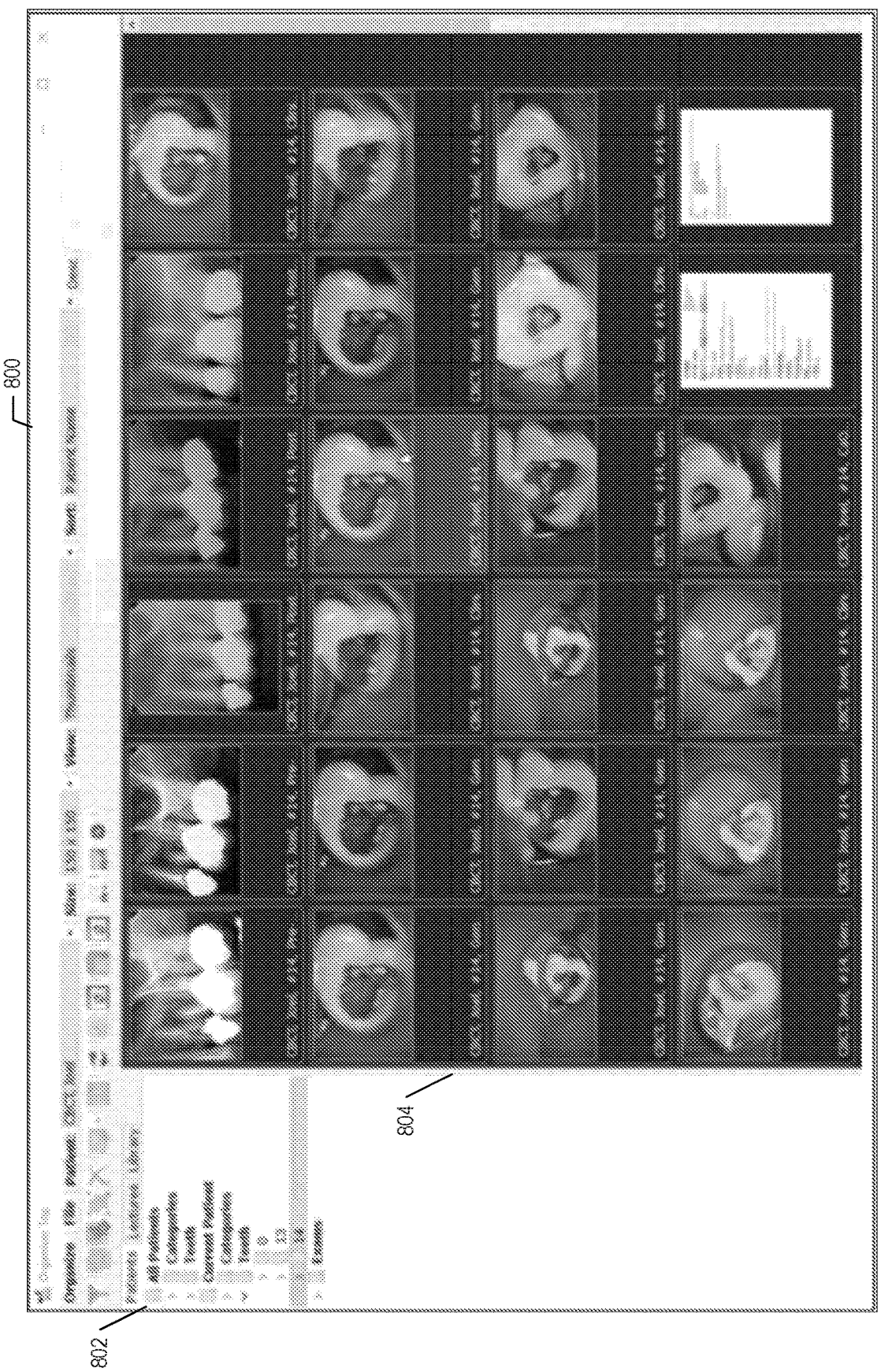

In FIG. 8A, a graphical user interface 800 of a practice management file organizer is depicted. The graphical user interface 800 includes a hierarchical directory selector 802 and a file organizer area 804. User selection of the user interface element 802 of FIG. 7 can cause the graphical user interface 800 of FIG. 8A to open. The files presented in the file organizer area 804 can be associated with the selected person in the graphical user interface 800 of FIG. 8. As shown, the presented files can include images, such as dental images for the person.

Figure 8B:
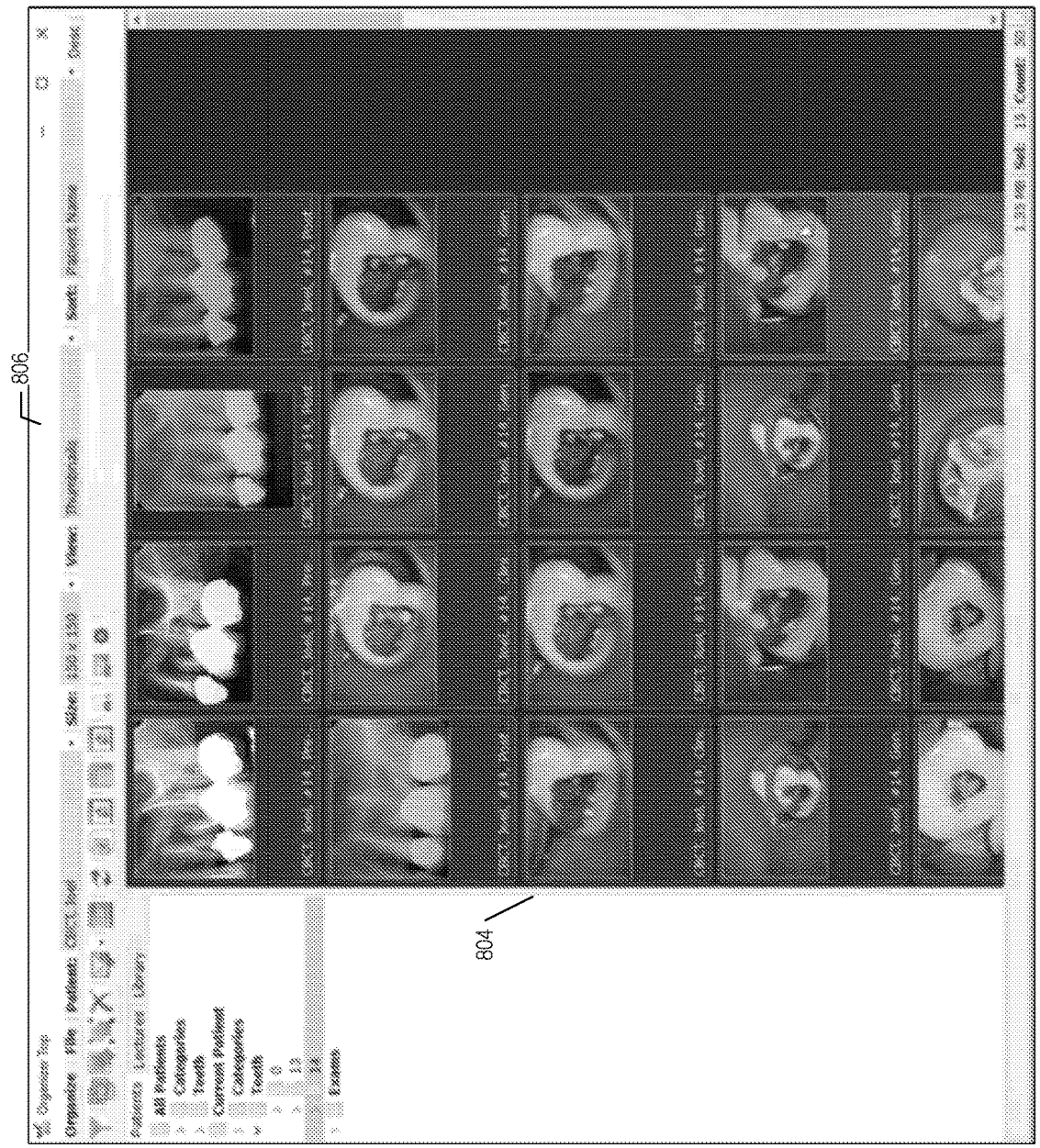

In FIG. 8B, another graphical user interface 806 of the practice management file organizer is depicted. The graphical user interface 806 of FIG. 8B can be similar to the graphical user interface 800 of FIG. 8A. As shown in the graphical user interface 806 of FIG. 8B, one or more files in the file organizer area 804 can be selected by a user. The user can then select a user interface element to initiate a graphical user interface for a collage image generator that receives the selected image files as input.

Figure 8C:
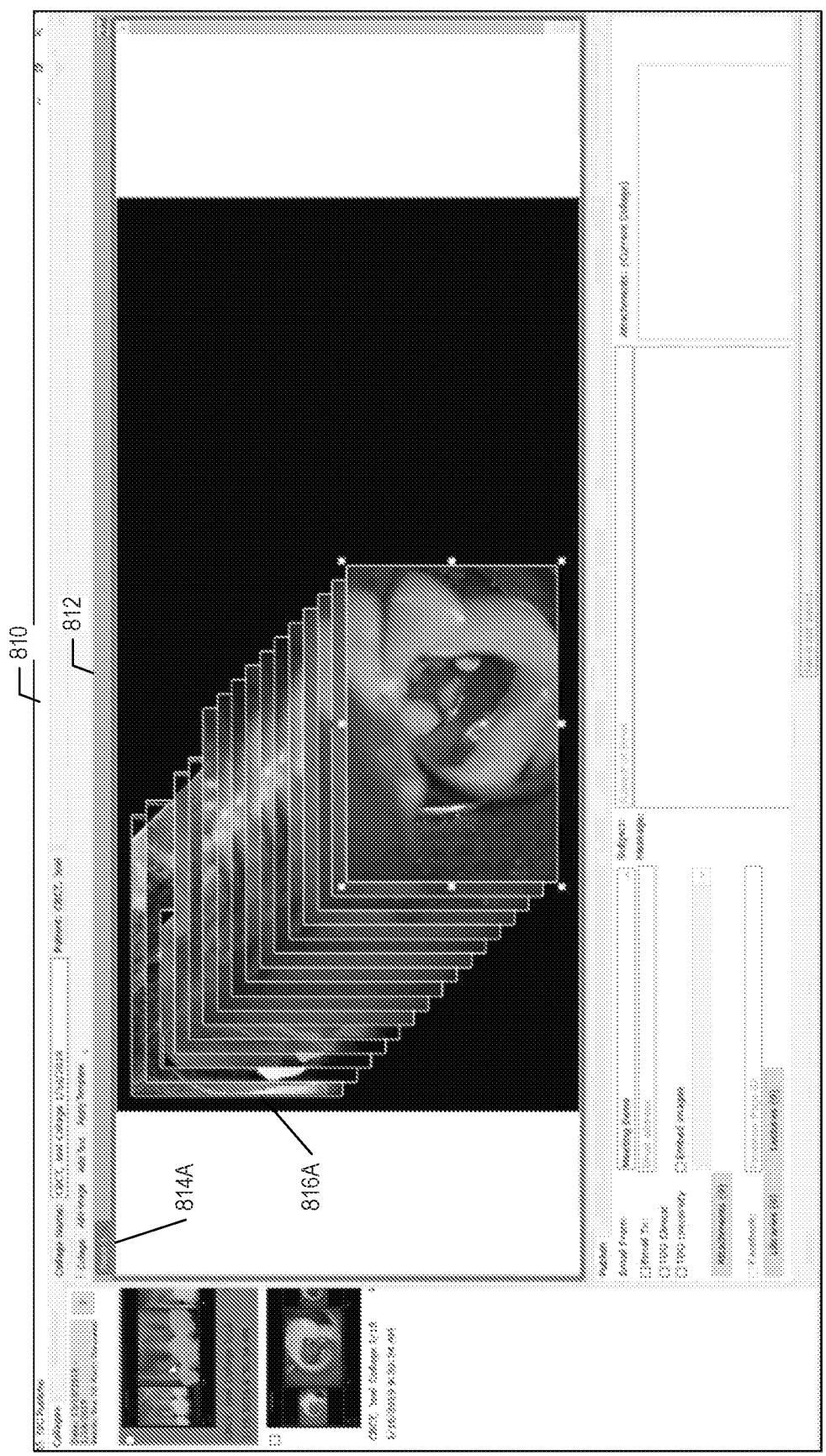

In FIG. 8C, a graphical user interface 810 of a collage image generator is depicted. The graphical user interface 810 can include a page area 812. The page area 812 can include one or more pages 814A. The one or more pages 816A can include multiple images 816A. The images 816A can be imported into the graphical user interface 810 from another application, such as the practice management file organizer. For example, the selected images from the graphical user interface 806 of FIG. 6B can be imported into the collage image generator. As described herein, a user can edit, manipulate, and/or arrange the images 816A. Each page of the one or more pages 814 can be output to a composite image that includes the images 816A.

Figure 8D:
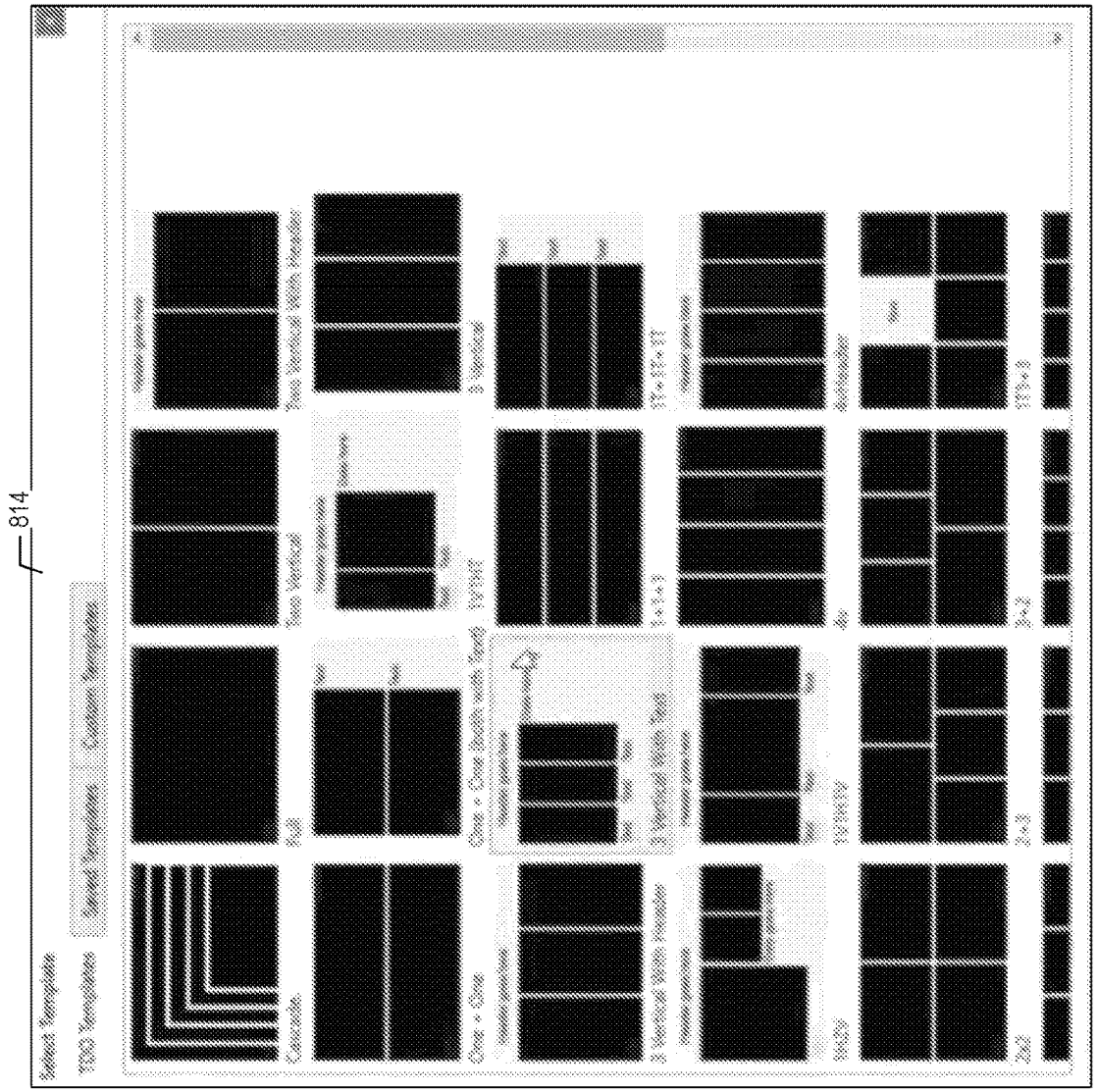

In FIG. 8D, another graphical user interface 814 of the collage image generator is depicted. The graphical user interface 814 can include or correspond to a template selector. User selection of one of the templates can cause the images in the collage image generator to arrange into the selected template format. If there are more images available than are specified in the template, then multiple pages may be generated from the images.

Figure 8E:
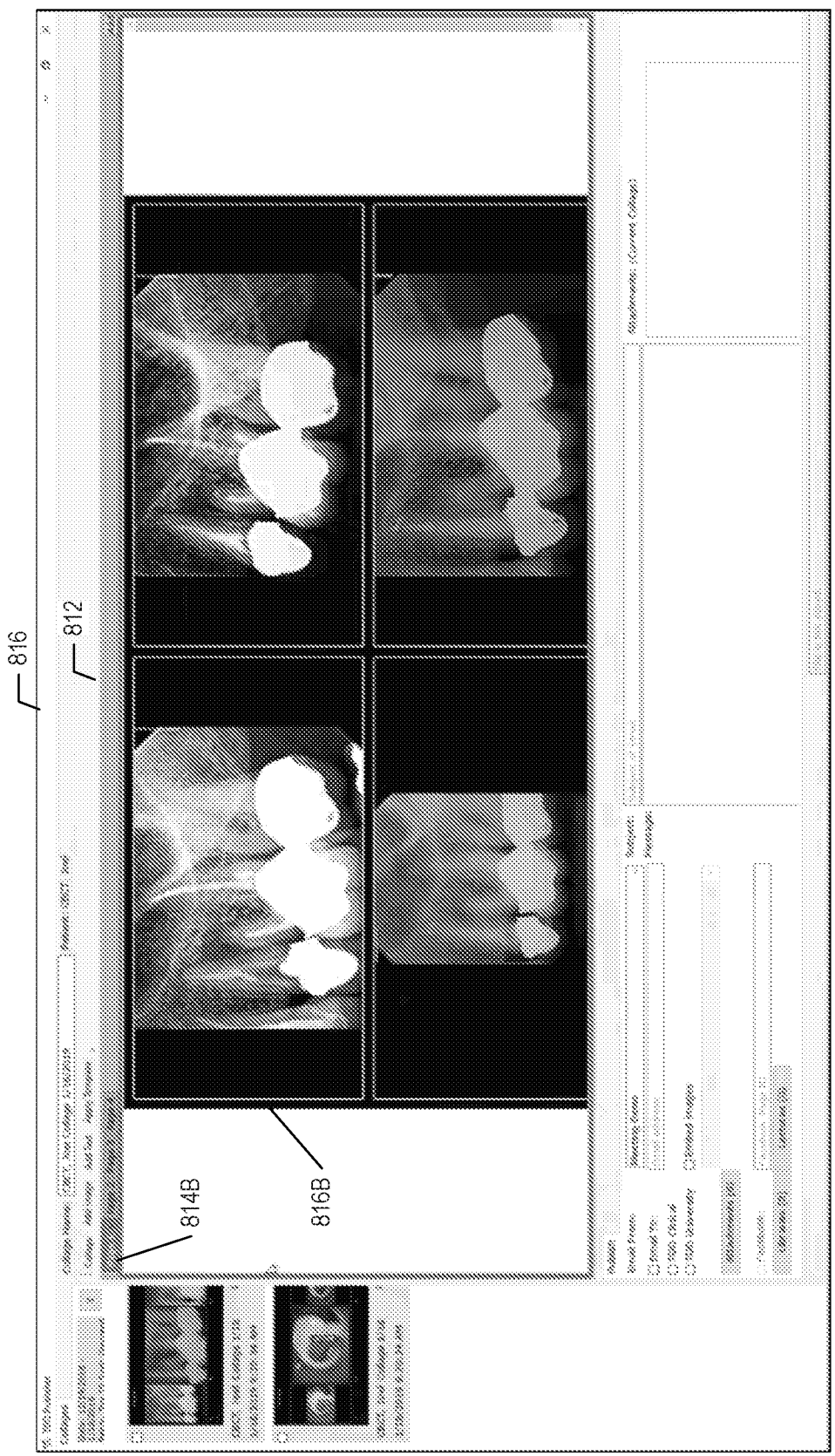

In FIG. 8E, a graphical user interface 810 of the collage image generator is depicted. The graphical user interface 816 of FIG. 8E can be similar to the graphical user interface 810 of FIG. 8C, The graphical user interface 816 can be presented in response to selection of a template from the graphical user interface 814 of FIG. 8D. The graphical user interface 816 can include the page area 812 and the page area 812 can include multiple pages, such as the first page 814B and additional one or more pages. The first page 814B can include a first subset of images 816B that are arranged according to the selected template. The remaining images can be assigned to the remaining pages. For example, if a selected image includes four slots for images and the set of images includes twenty images, then five pages may be generated with four images per page. In some embodiments, multiple templates can be applied to the set of images. For example, a first template may be applied to a first subset of images and a second template may be applied to a second subset of images. A user can select a different template and the arrangement of the images 816B may update accordingly.

Figure 8F:
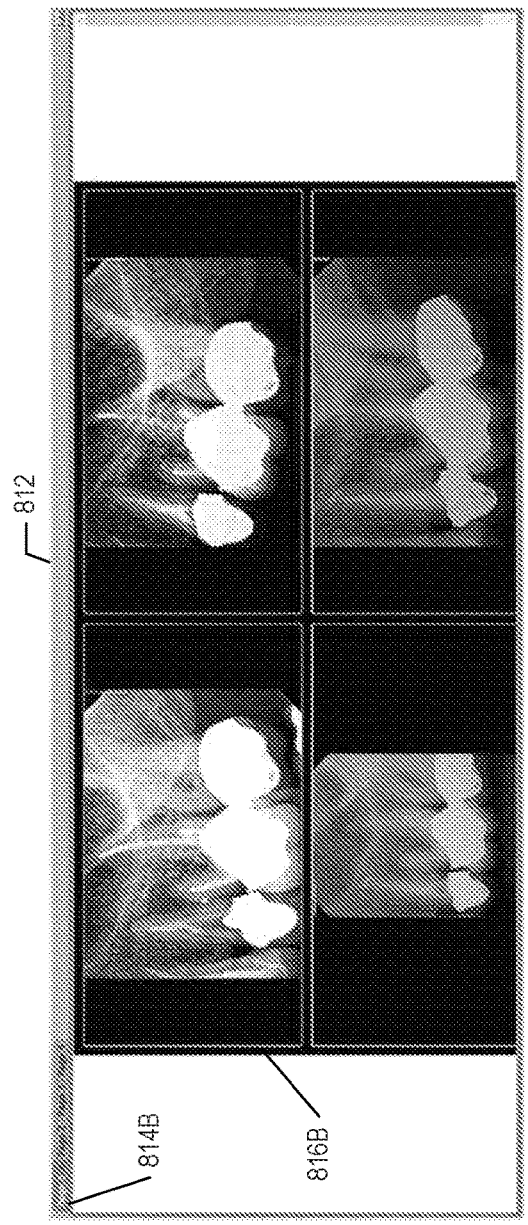
Figure 8G:
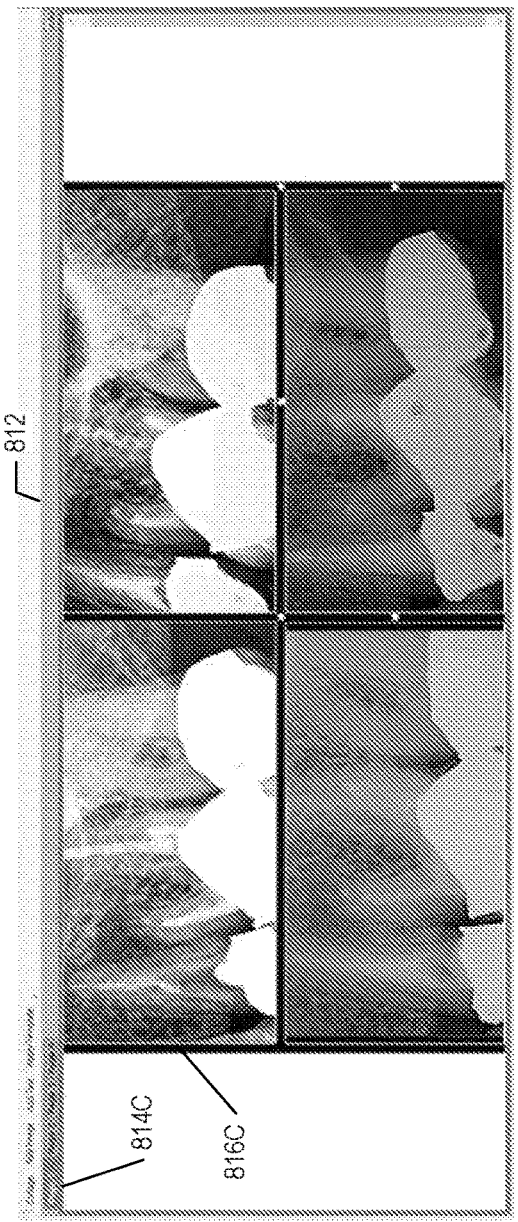

In FIGS. 8F and 8G, portions of a graphical user interface of the collage image generator are shown. In FIG. 8F, the page area 812 is depicted, which includes the first page 814B and the first subset of images 816B. In FIG. 8G, the page area 812 can be similar to the page area 812 of FIG. 8G. However, the page area 812 of FIG. 8G can include an updated first page 814C. The updated first page 814C can include an updated presentation of the first subset of images 816C. The updated presentation of the first subset of images 816C can be the result of a user interaction with the first subset of images 816B of FIG. 8F. For example, a user can interact with the first subset of images 816B of FIG. 8F to zoom in or out and/or to pan the images as shown in FIG. 8G.

Figure 8H:
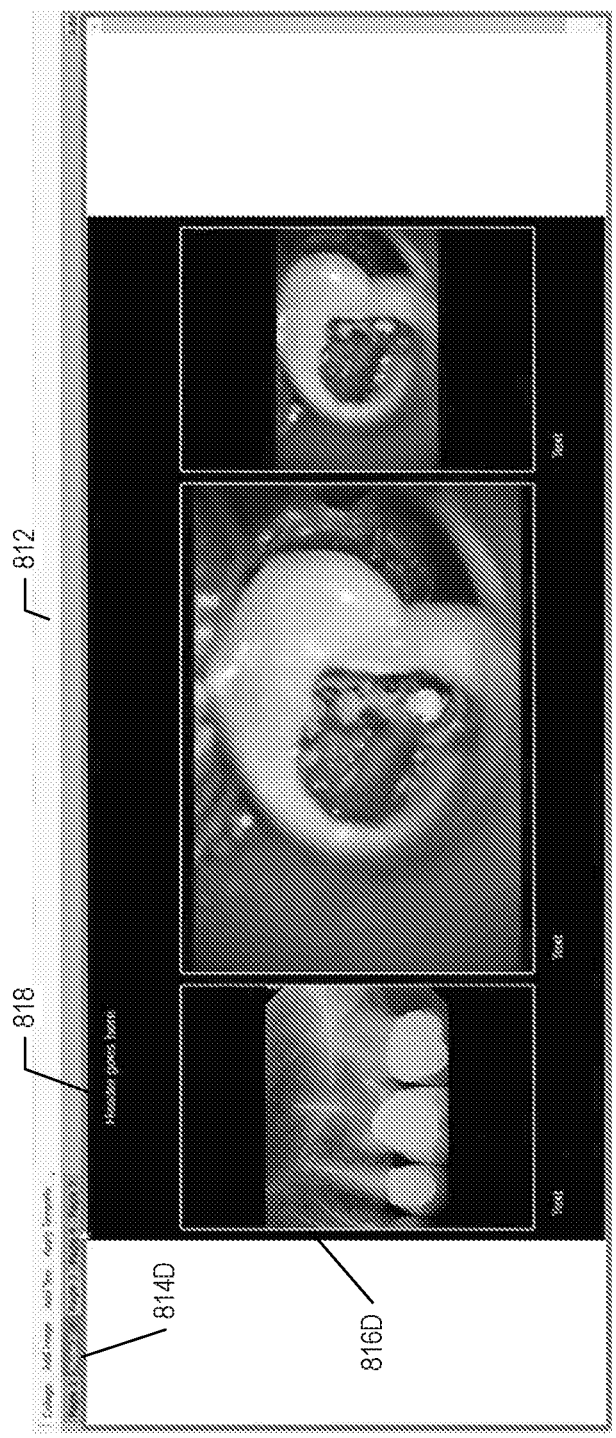
Figure 8I:
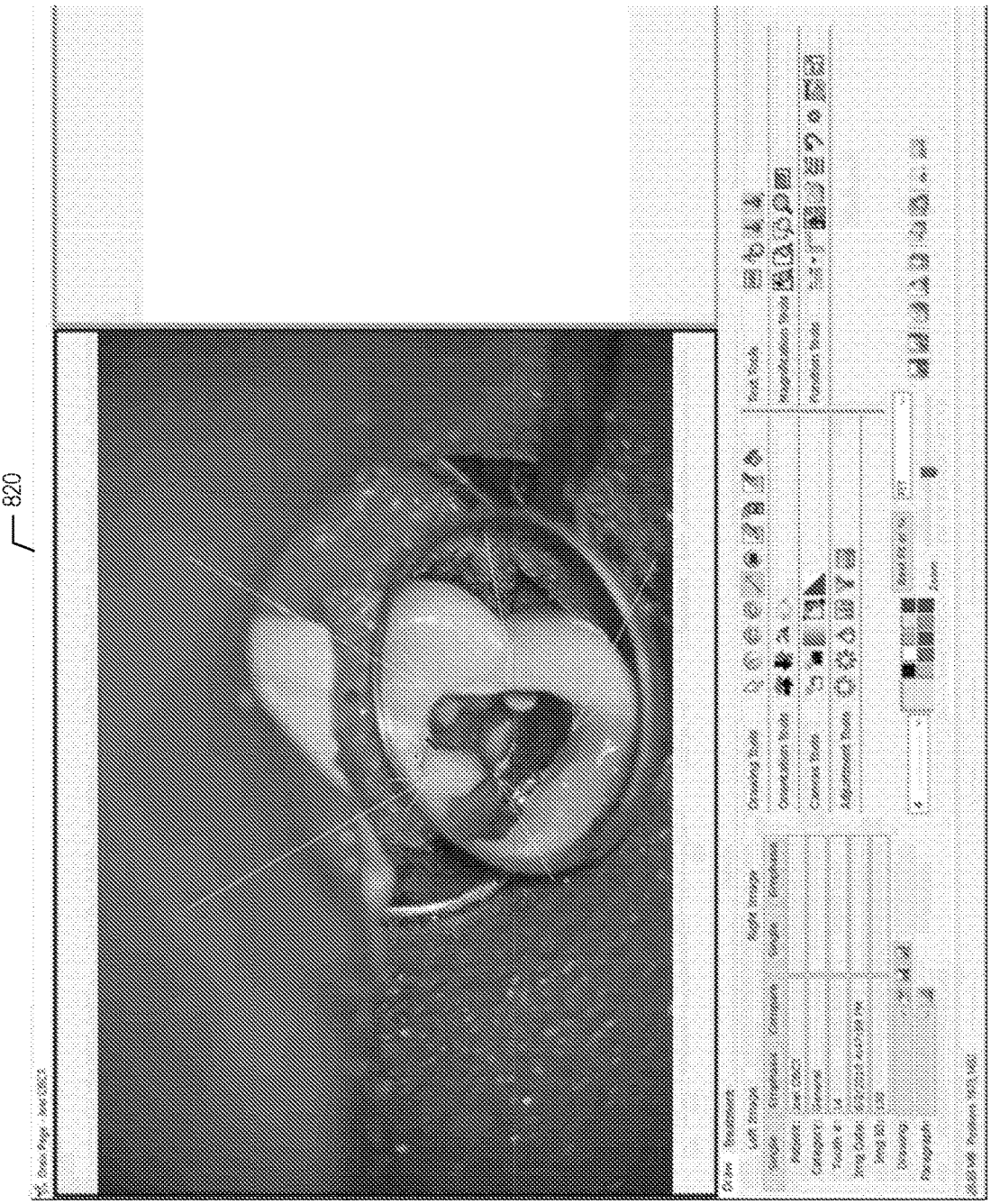

In FIG. 8H, another portion of a graphical user interface of the collage image generator is shown. The depicted page area 812 can include a second page 814D with a second subset of images 816D. The second page 814D can include editable user interface elements 818, such as editable text boxes or headings. In FIG. 8I, another graphical user interface 820 of the collage image generator is depicted. The graphical user interface 820 can enable a user to edit an image in a page of the collage image generator. For example, a user can add drawing elements or otherwise transform the image, which can be include in the composite image.

Figure 8J:
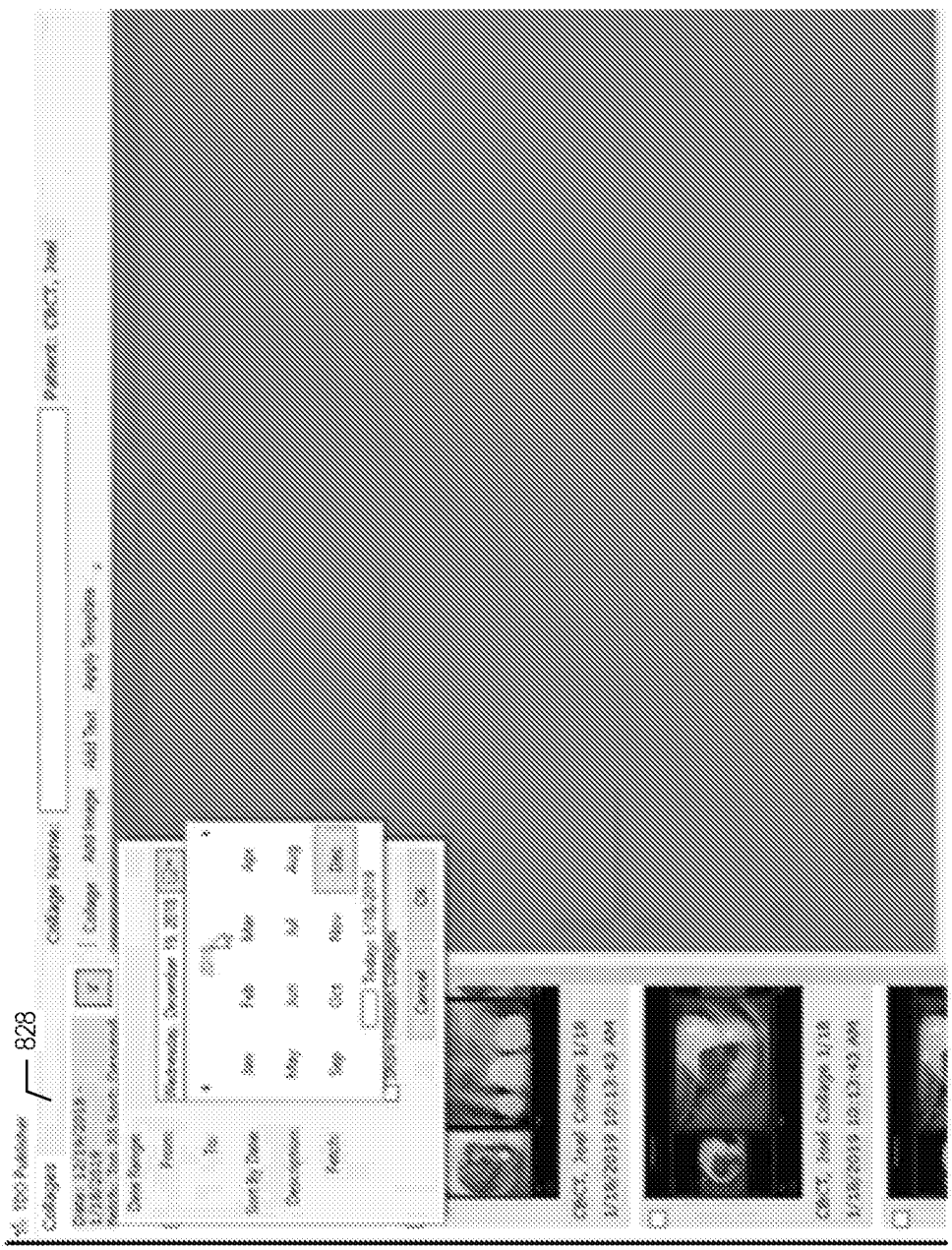

In FIG. 8J, another portion of a graphical user interface of the collage image generator is shown. The portion of the graphical user interface can include a search area 828. As shown, a user can search for saved collages by date range using the search area 828. The date range criteria may correspond to when the collage was created or when the individual image(s) were generated. In some embodiments, a user can search for generated collages by other search criteria, patient name, patient identifier, and/or a date range.

Figure 9:
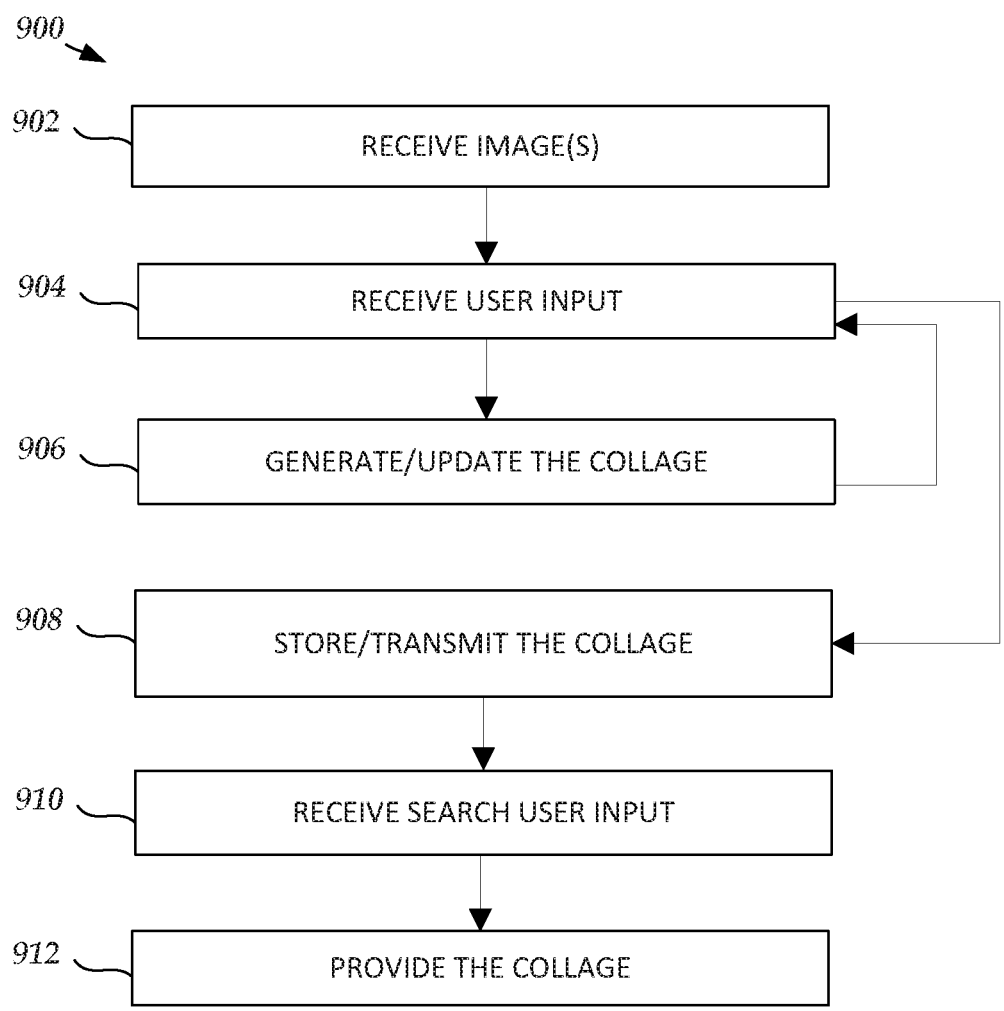
FIG. 9 depicts an example collage generation workflow, according to some embodiments of the present disclosure.

FIG. 9 is a flowchart of an example collage image generation method 900, according to some embodiments of the present disclosure. Although the method 900 is described in conjunction with the systems of FIG. 1B, any system configured to perform the method, in any order, is within the scope of this disclosure. The method 900 may be performed by the various components of the practice management database system 150 of FIG. 1B as discussed herein, including the collage image generator 158. Depending on the embodiment, the method 900 may include fewer or additional blocks and/or the blocks may be performed in an order different than is illustrated.

Beginning at block 902, images can be received. For example, the collage image generator 158 can receive one or more selected images. A user can select a person's images, which can be received by the collage image generator 158. A user can select images for a particular person that can be done through a file organizer, which is described above in further detail with respect to FIGS. 7, 8A, 8B, and 8C. The received images can originate from a dental or medical office that captured the images.

At block 904, user input can be received. For example, the collage image generator 158 can receive user input from a graphical user interface. Example user interactions can include, but are not limited to, selecting a template and/or manipulating images for a collage. Additional details regarding user interactions that can be received are described above in further detail with respect to FIGS. 8D, 8E, 8F, 8G, 8H, and 8I.

At block 906, a collage can be generated or updated. For example, the collage image generator 158 can generate or update a collage based on the received user input. If a template is selected, the collage image generator 158 can apply the selected template to one or more images. For example, a selection of a template with a number of slots for images (such as three) as applied to a set of images (such as nine total images) can cause the collage image generator 158 to generate a set of pages (such as three pages) that each include a subset of the images (such as three images each). The collage image generator 158 can calculate the number of pages and images per page based on the user input.

As shown, blocks 904 and 906 can continuously repeat. For example, subsequent user interactions can cause the generated collage to update. For example, pages can be added or removed. Multiple templates can be applied to the set of images in the same collage, such as a first template applied to a first subset of images and a second template applied to a second subset of images. At some point, received user input can cause the collage to be stored or transmitted at block 908. For example, a user can finish their editing and select a user interface element to save or export the generated collage.

At block 908, the collage can be stored or transmitted. The collage image generator 158 can output the image collage. In particular, example output can correspond to a single generated composite image for each page of the collage. For example, if the collage contains three pages with three images each, the output of the collage can be three composite images that can be saved as individual files. Based on the user input, the collage image generator 158 can store or transmit the output. For example, a user can select an upload option to transmit the generated composite images to another device or service, such as to a social media or forums application. In some embodiments, the output image collage can be stored in the image database 160. The collage image generator 158 can store metadata associated with the output image collage in in the image database 160. Example metadata includes a person, date, or case identifier associated with the output image collage.

At block 910, search user input can be received. For example, a user can retrieve a generated collage by specifying search parameters related to the output image collage, such as a date, person, or case parameter. The collage image generator 158 can execute a search query of the image database 160 to retrieve one or more output collages. At block 912, the retrieve output collage(s) can be provided to the user. Thus, an output collage can be saved and retrieved at a later date. In some embodiments, the output collage can be further edited and saved as a subsequent version or it can replace the old version of the output collage.

Additional Implementation Details and Embodiments

Figure 10:
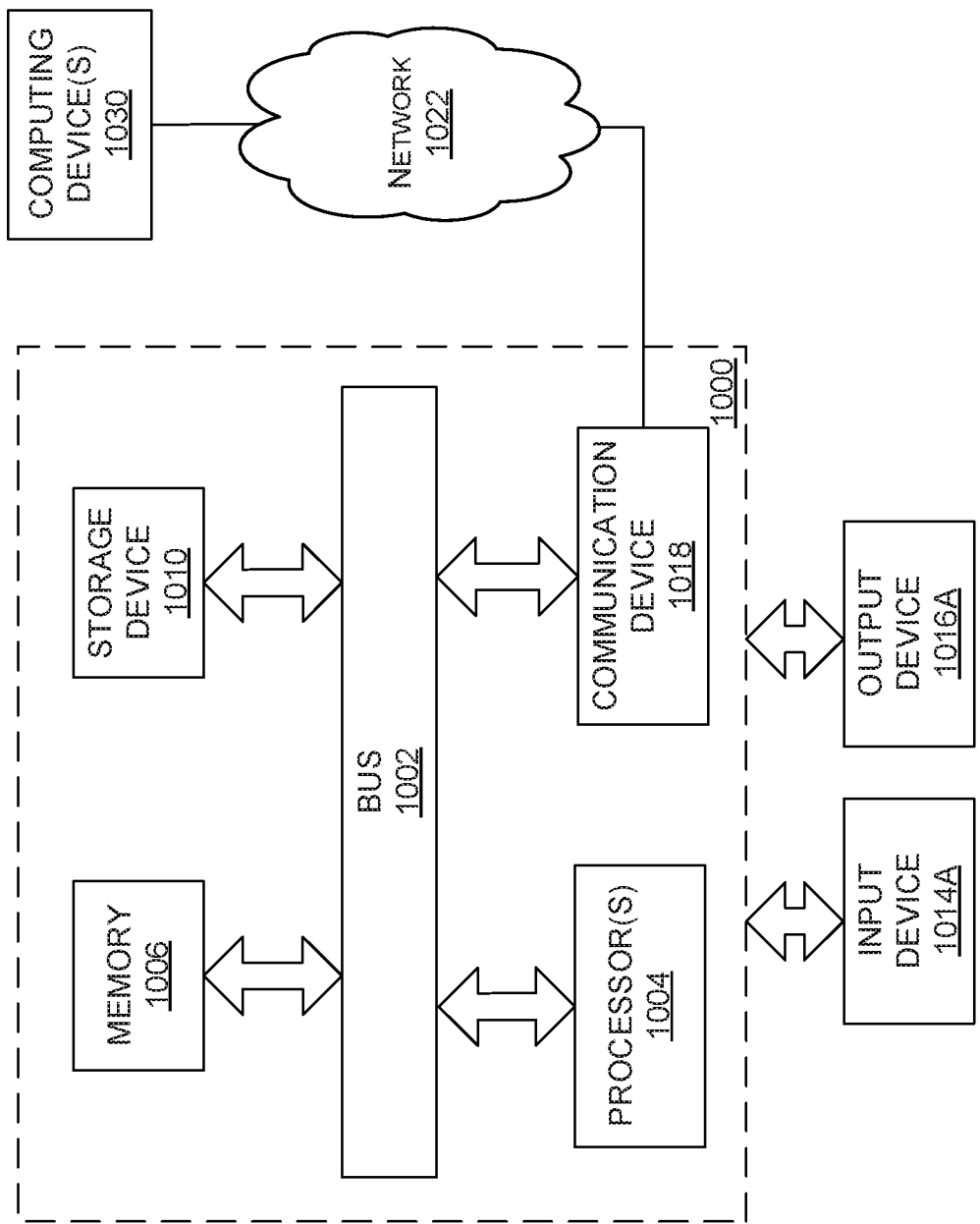
FIG. 10 illustrates an example computing system with which some embodiments of the present disclosure may be implemented.

FIG. 10 depicts a general architecture of a computing system 1000. The computing system 1000 or components of the computing system 800 may be used to implement by any of the devices or components discussed herein, such as the scheduling database system 100, the scheduling service 106, the scheduling server 108, the practice management database system 158, and/or the collage image generator 158, The general architecture of the computing system 1000 depicted in FIG. 10 includes an arrangement of computer hardware and software components that may be used to implement aspects of the present disclosure. The computing system 1000 may include many more (or fewer) elements than those shown in FIG. 10. It is not necessary, however, that all of these elements be shown in order to provide an enabling disclosure. As illustrated, the computing system 1000 includes one or more hardware processors 1004, a communication interface 1018, a computer readable medium storage device 1010, one or more input devices 1014A (such as a touch screen, mouse, keyboard, etc.), one or more output devices 1016A (such as a monitor, screen, or display), and memory 1006, some of which may communicate with one another by way of a communication bus 1002 or otherwise. The communication interface 1018 may provide connectivity to one or more networks or computing systems. The hardware processor(s) 1004 may thus receive information and instructions from other computing systems or services via the network 1022.

The memory 1006 may contain computer program instructions (grouped as modules or components in some embodiments) that the hardware processor(s) 1004 executes in order to implement one or more embodiments. The memory 1006 generally includes RAM, ROM or other persistent, auxiliary or non-transitory computer-readable media. The memory 1006 may store an operating system that provides computer program instructions for use by the hardware processor(s) 1004 in the general administration and operation of the computing system 1000. The memory 1006 may further include computer program instructions and other information for implementing aspects of the present disclosure. In addition, memory 1006 may include or communicate with the storage device 1010. A storage device 1010, such as a magnetic disk, optical disk, or USB thumb drive (Flash drive), etc., is provided and coupled to the bus 1002 for storing information, data, or instructions.

The memory 1006 also may be used for storing temporary variables or other intermediate information during execution of instructions to be executed by hardware processor(s) 1004. Such instructions, when stored in storage media accessible to hardware processor(s) 1004, render the computing system 1000 into a special-purpose machine that is customized to perform the operations specified in the instructions.

In general, the word "instructions," as used herein, refers to logic embodied in hardware or firmware, or to a collection of software modules, possibly having entry and exit points, written in a programming language, such as, but not limited to, Java, Scala, Lua, C, C++, or C#. A software module may be compiled and linked into an executable program, installed in a dynamic link library, or may be written in an interpreted programming language such as, but not limited to, BASIC, Perl, or Python. It will be appreciated that software modules may be callable from other modules or from themselves, or may be invoked in response to detected events or interrupts. Software modules configured for execution on computing devices by their hardware processor(s) may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, or may be comprised of programmable units, such as programmable gate arrays or processors. The modules or computing device functionality described herein are preferably implemented as software modules, but may be represented in hardware or firmware. Generally, the instructions described herein refer to logical modules that may be combined with other modules or divided into sub-modules despite their physical organization or storage.

The term "non-transitory media," and similar terms, as used herein refers to any media that store data or instructions that cause a machine to operate in a specific fashion. Such non-transitory media may comprise non-volatile media or volatile media. Non-volatile media includes, for example, optical or magnetic disks, such as the storage device 1010. Volatile media includes dynamic memory, such as the main memory 1006. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise the bus 1002. Transmission media can also take the form of acoustic or light waves, such as those generated during radio-wave and infra-red data communications.

The computing system 1000 also includes a communication interface 1018 coupled to the bus 1002. The communication interface 818 provides a two-way data communication to the network 1022. For example, communication interface sends and receives electrical, electromagnetic, or optical signals that carry digital data streams representing various types of information via cellular, packet radio, GSM, GPRS, CDMA, WiFi, satellite, radio, RF, radio modems, ZigBee, XBee, XRF, XTend, Bluetooth, WPAN, line of sight, satellite relay, or any other wireless data link.

The computing system 1000 can send messages and receive data, including program code, through the network 1022 and the communication interface 1018. A computing system 1000 may communicate with other computing devices 1030 via the network 1022.

The computing system 1000 may include a distributed computing environment including several computer systems that are interconnected using one or more computer networks. The computing system 1000 could also operate within a computing environment having a fewer or greater number of devices than are illustrated in FIG. 10.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A hardware processor can include electrical circuitry or digital logic circuitry configured to process computer-executable instructions. In another embodiment, a processor includes an FPGA, other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed:

1. A method comprising:
   receiving, via a first scheduling input user interface, first login information;
   determining a first profile associated with the first login information;
   receiving, via the first scheduling input user interface, a first scheduling search preference;
   determining, from a plurality of entities, a first subset of entities according to the first scheduling search preference, wherein to determine the first subset of entities further comprises:
      determining that the first profile lacks authorization for a first entity of the plurality of entities, wherein the first subset of entities excludes the first entity;
   retrieving first scheduling data for the first subset of entities;
   causing presentation of a first scheduling user interface, wherein the first scheduling user interface presents the first scheduling data;
   receiving, via a second scheduling input user interface, second login information;
   determining a second profile associated with the second login information;
   receiving, via the second scheduling input user interface, a second scheduling search preference;
   determining, from the plurality of entities, a second subset of entities according to the second scheduling search preference, wherein to determine the second subset of entities further comprises:
      determining that the second profile has authorization for the first entity, wherein the second subset of entities comprises the first entity;
   retrieving second scheduling data for the second subset of entities that includes the first entity; and
   causing presentation of a second scheduling user interface, wherein the second scheduling user interface presents the second scheduling data.

2. The method of claim 1, further comprising:
   receiving, via the second scheduling user interface, a scheduling selection for the first entity;
   determining that an attempted connection with the first entity has a failed status; and
   storing, in a first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

3. The method of claim 2, further comprising:
  determining to synchronize the first scheduling entry based at least in part on the first synchronization status of the first scheduling entry; and
  causing a second scheduling entry to be stored or updated in a second data store of the first entity, the second scheduling entry corresponding to the first scheduling entry.

4. The method of claim 1, further comprising:
  receiving, via the second scheduling user interface, a scheduling selection for the first entity;
  storing, in a first data store, a first scheduling entry for the first entity according to the scheduling selection, wherein the first scheduling entry further comprises a first synchronization status;
  determining to synchronize the first scheduling entry based at least n part on the first synchronization status of the first scheduling entry; and
  causing a second scheduling entry to be stored or updated in a second data store of the first entity, the second scheduling entry corresponding to the first scheduling entry.

5. The method of claim 4, further comprising:
  setting, in the first data store, a first field in a third scheduling entry to a second synchronization status, wherein the second synchronization status marks the third scheduling entry for a synchronization check from an entity to the first data store;
  determining that the third scheduling entry has a corresponding entry in the second data store of the first entity; and
  updating; in the first data store, the first field in the third scheduling entry from the second synchronization status to a third synchronization status, the third synchronization status indicating a synchronization complete status.

6. The method of claim 5, further comprising:
  setting, in the first data store, a second field in a fourth scheduling entry to the second synchronization status;
  determining that an entry in the second data store of the first entity does not exist that corresponds to the fourth scheduling entry;
  determining to preserve the third scheduling entry based at least in part on the first field being set to the third synchronization status;
  determining to delete the fourth scheduling entry based at least in part on the second field being set to the second synchronization status; and
  deleting, in the first data store, the fourth scheduling entry.

7. A system comprising:
  a non-transitory computer storage medium configured to at least store computer-executable instructions; and
  one or more computer hardware processors in communication with the non-transitory computer storage medium, the one or more computer hardware processors configured to execute the computer-executable instructions to at least:
    receive, via a first scheduling input user interface, first login information;
    determine a first profile associated with the first login information;
    receive, via the first scheduling input user interface, a first scheduling search preference;
    determine, from a plurality of entities, a first subset of entities according to the first scheduling search preference, wherein to determine the first subset of entities further comprises:
      determine that the first profile lacks authorization for a first entity of the plurality of entities, wherein the first subset of entities excludes the first entity;
    retrieve first scheduling data for the first subset of entities;
    cause presentation of a first scheduling user interface comprising the first scheduling data;
    receive, via a second scheduling input user interface, second login information;
    determine a second profile associated with the second login information;
    receive, via the second scheduling input user interface, a second scheduling search preference;
    determine, from the plurality of entities, a second subset of entities according to the second scheduling search preference, wherein to determine the second subset of entities further comprises:
      determine that the second profile has authorization for the first entity, wherein the second subset of entities comprises the first entity;
    retrieve second scheduling data for the second subset of entities that includes the first entity; and
    cause presentation of a second scheduling user interface comprising the second scheduling data.

8. The system of claim 7, wherein to determine that the first profile lacks authorization for the first entity further comprises:
  determine that the first profile corresponds to a profile for a person.

9. The system of claim 7, wherein to determine that the second profile has authorization for the first entity further comprises:
  determine that the second profile corresponds to a general practitioner.

10. The system of claim 7, wherein to determine that the second profile has authorization for the first entity further comprises:
  determine that the second profile corresponds to at least one preferred referrer for the first entity.

11. The system of claim 7, wherein the first entity corresponds to a special practitioner.

12. The system of claim 7, further comprising a first data store; wherein the one or more computer hardware processors are further configured to:
  receive, via the second scheduling user interface, a scheduling selection for the first entity;
  determine that an attempted connection with the first entity has a failed status; and
  store, in a first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

13. The system of claim 12, the one or more computer hardware processors are further configured to:
  determine to synchronize the first scheduling entry based at least in part on the first synchronization status of the first scheduling entry; and
  cause a second scheduling entry to be stored or updated in a second data store of the first entity, the second scheduling entry corresponding to the first scheduling entry.

14. A system comprising:
  a non-transitory computer storage medium configured to at least store computer-executable instructions; and one or more computer hardware processors in communication with the non-transitory computer storage medium, the one or more computer hardware processors configured to execute the computer-executable instructions to at least:
- receive, via a scheduling input user interface, login information;
- determine a profile associated with the login information;
- receive, via the scheduling input user interface, a scheduling search preference;
- determine, from a plurality of entities, a subset of entities according to the scheduling search preference, wherein to determine the subset of entities further comprises:
  - determine that the profile has authorization for a first entity,
- wherein the subset of entities comprises the first entity;
- retrieve scheduling data for the subset of entities that includes the first entity; and
- cause presentation of a scheduling user interface, wherein the scheduling user interface presents the scheduling data.

15. The system of claim 14, further comprising a first data store, wherein the one or more computer hardware processors are further configured to:
- receive, via the scheduling user interface, a scheduling selection for the first entity;
- determine that an attempted connection with the first entity has a failed status; and
- store, in the first data store, a first scheduling entry for the first entity according to the scheduling selection, wherein the first scheduling entry further comprises a first synchronization status based at least in part on the failed status of the attempted connection, and wherein the first synchronization status marks the first scheduling entry for future propagation to the first entity.

16. The system of claim 15, wherein the one or more computer hardware processors are further configured to:
- determine to synchronize the first scheduling entry based at least in part on the first synchronization status of the first scheduling entry; and
- cause a second scheduling entry to be stored or updated in a second data store of the first entity, the second scheduling entry corresponding to the first scheduling entry.

17. The system of claim 14, further comprising a first data store, wherein the one or more computer hardware processors are further configured to:
- receive, via the scheduling user interface, a scheduling selection for the first entity;
- store, in the first data store, a first scheduling entry for the first entity according to the scheduling selection, wherein the first scheduling entry further comprises a first synchronization status;
- determine to synchronize the first scheduling entry based at least in part on the first synchronization status of the first scheduling entry; and
- cause a second scheduling entry to be stored or updated in a second data store of the first entity, the second scheduling entry corresponding to the first scheduling entry.

18. The system of claim 17, wherein the one or more computer hardware processors are further configured to:
- set, in the first data store, a first field in a third scheduling entry to a second synchronization status, wherein the second synchronization status marks the third scheduling entry for a synchronization check from an entity to the first data store;
- determine that the third scheduling entry has a corresponding entry in the second data store of the first entity; and
- update, in the first data store, the first field in the third scheduling entry from the second synchronization status to a third synchronization status, the third synchronization status indicating a synchronization complete status.

19. The system of claim 18, wherein the one or more computer hardware processors are further configured to:
- set, in the first data store, a second field in a fourth scheduling entry to the second synchronization status;
- determine that an entry in the second data store of the first entity does not exist that corresponds to the fourth scheduling entry;
- determine to delete the fourth scheduling entry based at least in part on the second field being set to the second synchronization status; and
- delete, in the first data store, the fourth scheduling entry.

20. The system of claim 14, wherein to determine that the profile has authorization for the first entity further comprises:
- determine that the profile corresponds to a general practitioner.

* * * * *